(12) United States Patent
Roenneburg et al.

(10) Patent No.: US 7,937,502 B2
(45) Date of Patent: May 3, 2011

(54) INSTRUMENTATION CONTROL SOFTWARE

(75) Inventors: Luke D. Roenneburg, Albany, WI (US);
Gregory J. Robinson, Sun Prairie, WI (US); Kirby S. Reed, Madison, WI (US); Christian Zander, Hudson, WI (US)

(73) Assignee: Gilson, Inc., Middleton, WI (US)

( * ) Notice: Subject to any disclaimer, the term of this patent is extended or adjusted under 35 U.S.C. 154(b) by 1384 days.

(21) Appl. No.: 11/217,084

(22) Filed: Aug. 31, 2005

(65) Prior Publication Data

US 2006/0048846 A1   Mar. 9, 2006

Related U.S. Application Data

(60) Provisional application No. 60/606,277, filed on Sep. 1, 2004.

(51) Int. Cl.
*G06F 3/00* (2006.01)
(52) U.S. Cl. .................................. 710/5; 710/8; 710/14
(58) Field of Classification Search ........................ 710/5
See application file for complete search history.

(56) References Cited

U.S. PATENT DOCUMENTS

| | | | |
|---|---|---|---|
| 6,666,065 B2 | 12/2003 | Gilson et al. | |
| 7,149,905 B2 * | 12/2006 | Brown et al. | ................. 713/300 |
| 2002/0062287 A1 * | 5/2002 | Katz et al. | ........................ 705/51 |
| 2002/0178779 A1 * | 12/2002 | Gilson et al. | .................... 73/1.74 |
| 2002/0182046 A1 * | 12/2002 | Schempf et al. | .............. 414/623 |
| 2003/0074523 A1 * | 4/2003 | Johnson | ......................... 711/112 |
| 2004/0220780 A1 * | 11/2004 | Linley et al. | .................. 702/188 |
| 2004/0240328 A1 * | 12/2004 | Chiba et al. | ................... 369/30.1 |

OTHER PUBLICATIONS

Clyde Hoadley. "A Very Short Introduction to UNIX"; Apr. 30, 2002; Metropolitan State College of Denver Information Technology Center for Technology Services; v1.0; pp. 9-11; http://clem.mscd.edu/~hoadleyc/papers/ShortIntroductionToUNIX.pdf.*

* cited by examiner

*Primary Examiner* — Henry W Tsai
*Assistant Examiner* — John B Roche
(74) *Attorney, Agent, or Firm* — Foley & Lardner LLP

(57) ABSTRACT

A controller controls a sequence of actions at a device. The controller includes computer instructions that receive a plurality of user inputs and command information associated with an action for the device to perform. The first user input defines a target in a bed layout of the device. The second user input assigns the target to a first zone of the bed layout. The third user input assigns the target to a second zone of the bed layout. The fourth user input indicates an operational mode for controlling performance of the action. The operational mode includes a non-validation mode defining a state of operation wherein a device limitation is not imposed to restrict the action. The command information includes a command name identifying the action and a device identifier. A unique command method corresponding to the device identifier and to the command name is identified and executed to control operation of the device as it performs the action at the defined target without imposing the device limitation if the fourth user input indicates the non-validation mode.

27 Claims, 18 Drawing Sheets

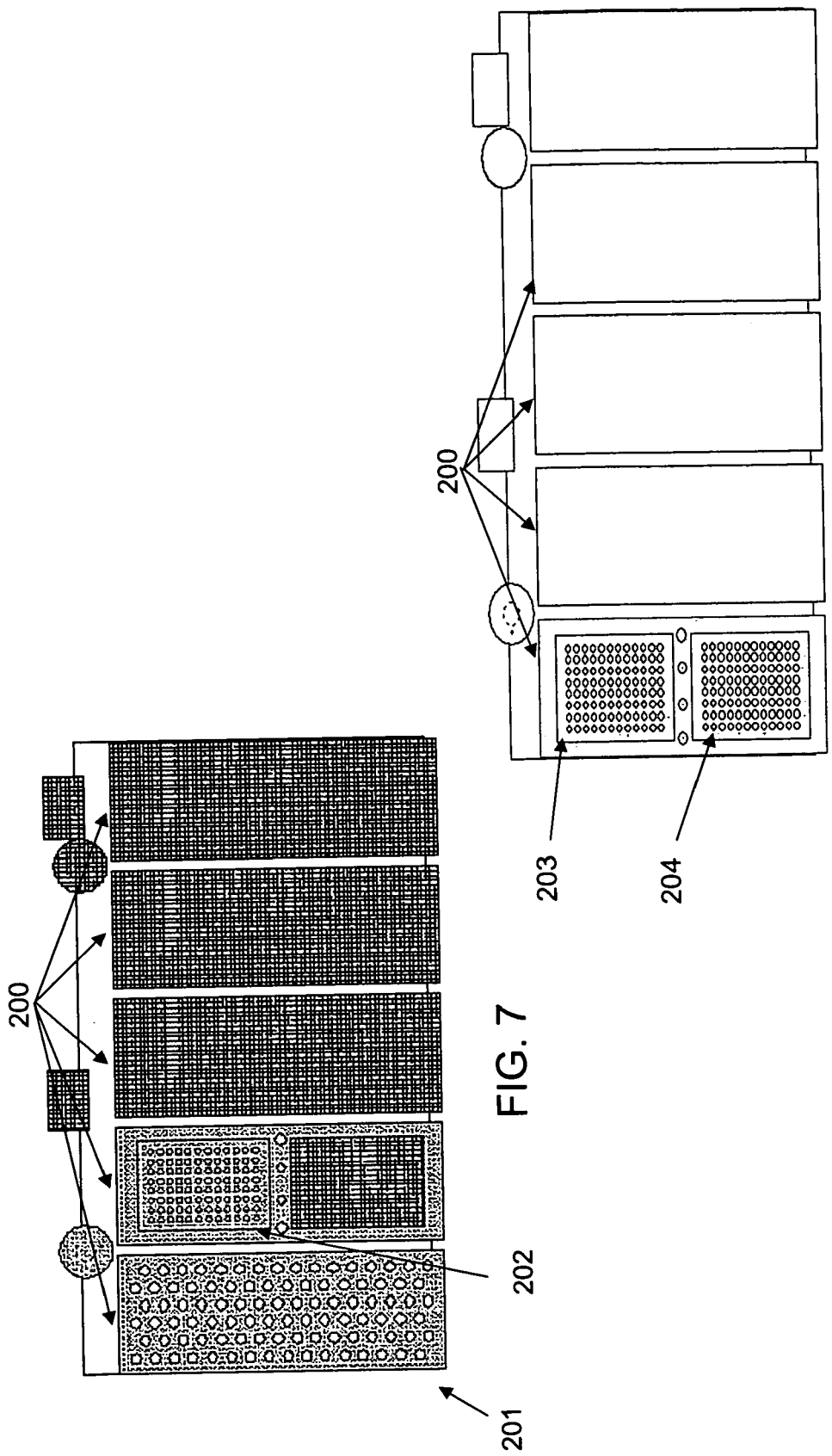

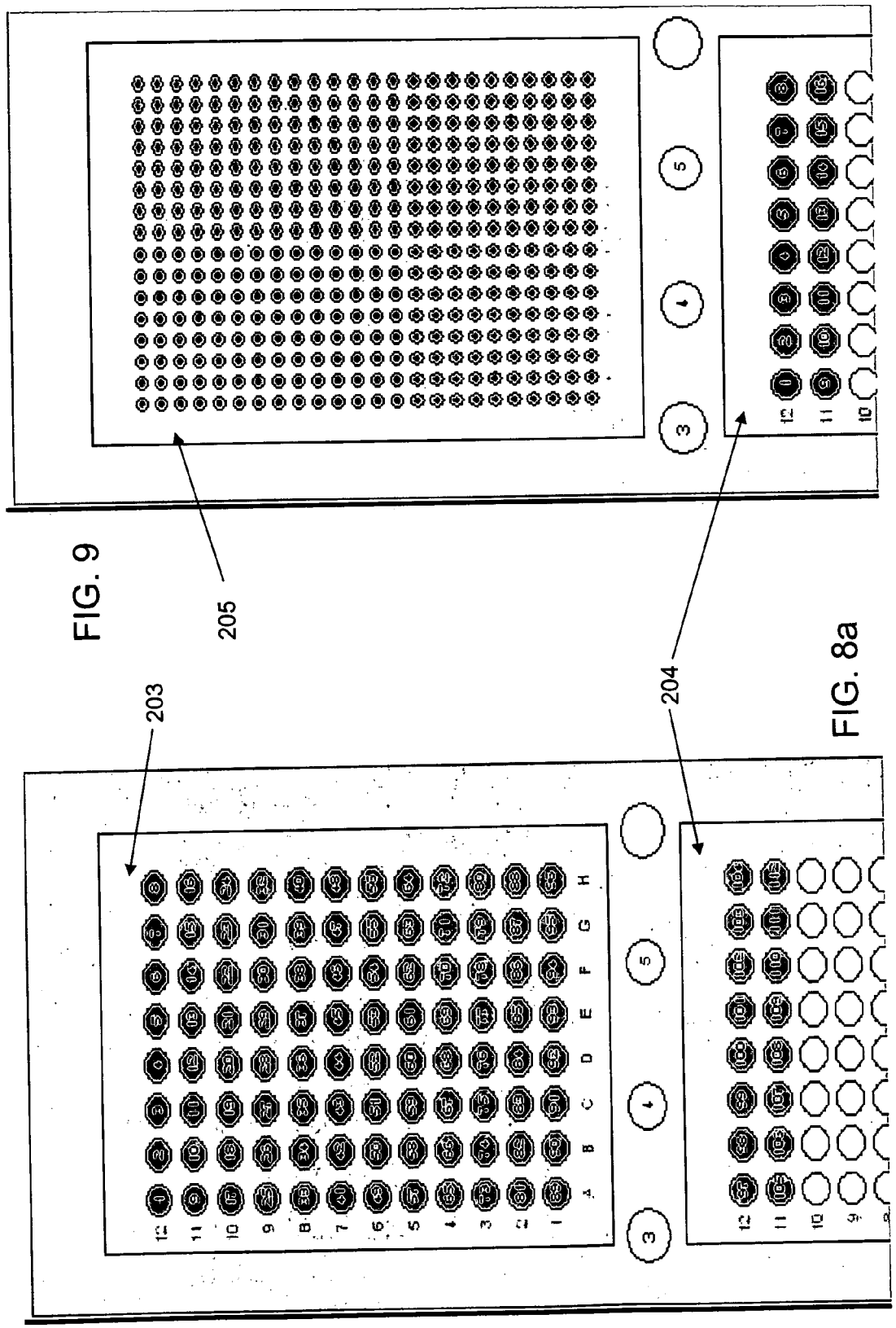

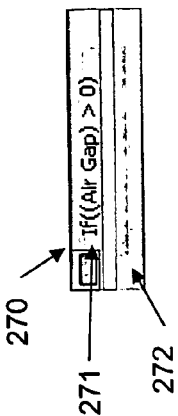
FIG. 19
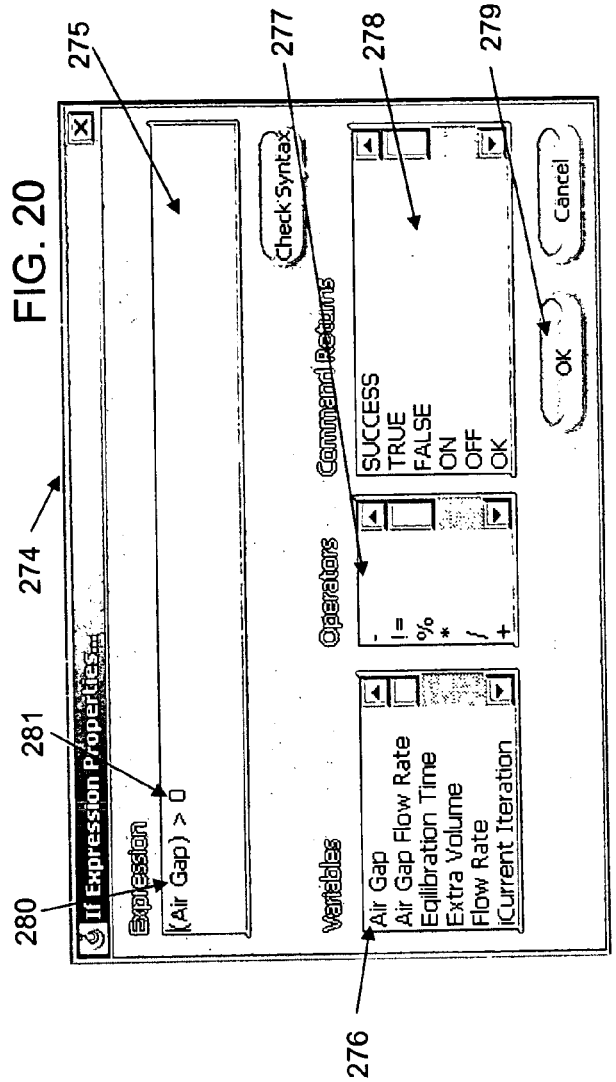
FIG. 20
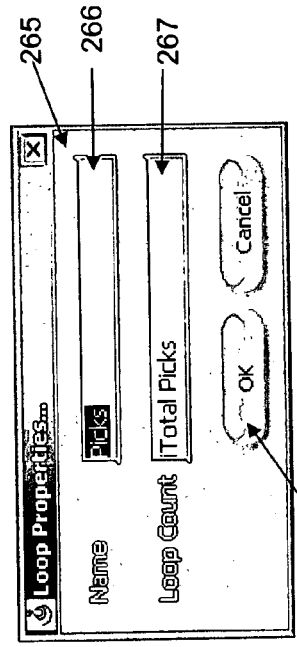
FIG. 18
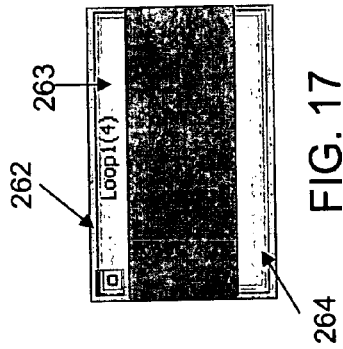
FIG. 17
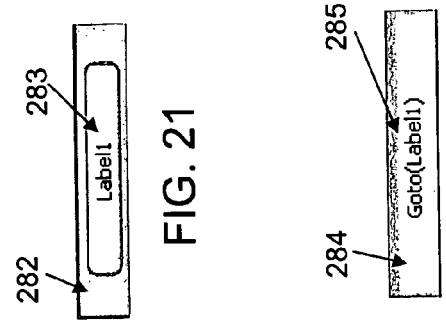
FIG. 21
FIG. 22

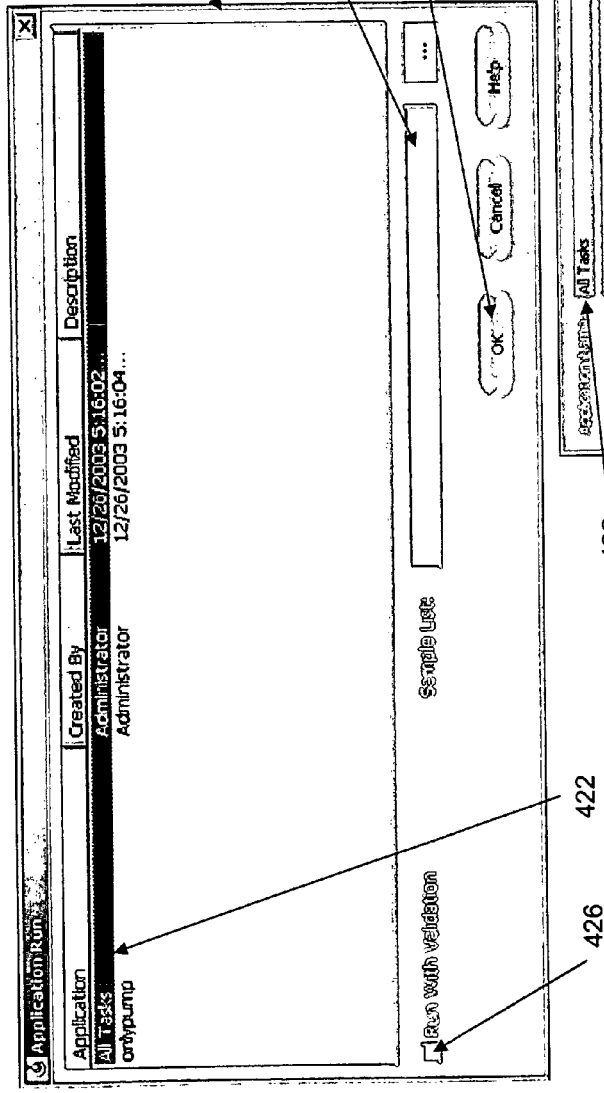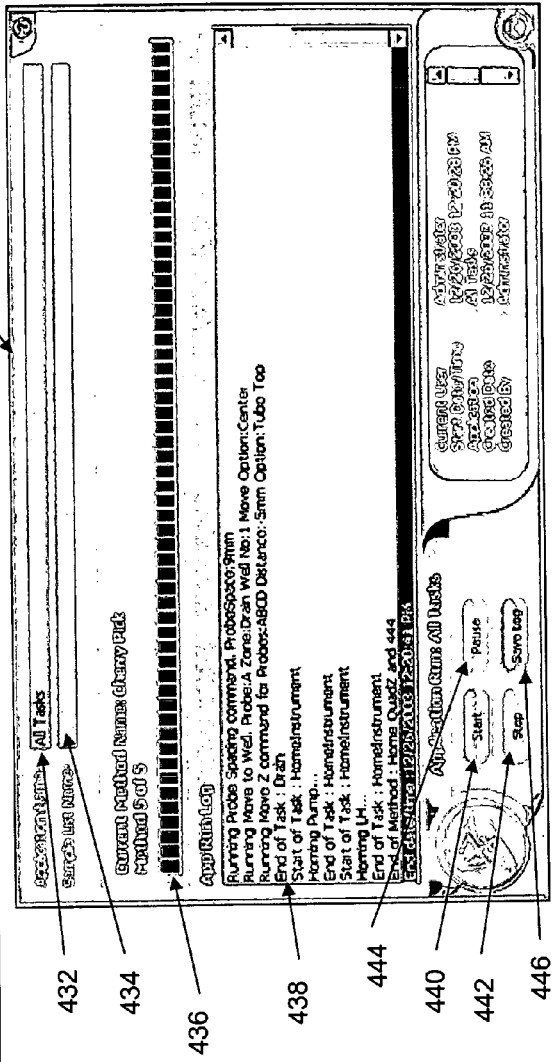

INSTRUMENTATION CONTROL SOFTWARE

FIELD OF THE INVENTION

The present invention is related generally to the automation of instrumentation usage. More specifically, the present invention relates to control software for automating the instrumentation usage.

BACKGROUND OF THE INVENTION

In pharmaceutical, genomic, and proteomic research, drug development laboratories, and other biotechnology applications, automated liquid handlers are used to handle laboratory samples in a variety of laboratory procedures. For example, liquid handlers are used for biotechnological and pharmaceutical liquid assay procedures, compound distribution, microarray manufacturing, sample preparation for high pressure liquid chromatography, etc. An automated liquid handler has a bed that supports an array of sample receptacles such as tubes in one or more racks or an array of numerous sample containing wells in one or more microplates. For example, racks may be arranged to hold ninety-six receptacles arranged in an eight by twelve array, three hundred eighty-four receptacles arranged in a sixteen by twenty-four array, etc.

A typical liquid handler has a probe or an array of multiple probes that are moved into alignment with one or more receptacles placed in the bed. The probe performs liquid handling operations such as removing liquid from or adding liquid to the receptacles. The probe or probe array is generally carried on a support arm that may be movable in X, Y, and Z directions. An X-direction track may be provided along with a first carriage movable along the track to facilitate movement in the X-direction. A Y-axis track may be mounted on the first carriage, with a second carriage movable along this Y-axis track. A Z-axis track may in turn be carried by the second carriage, with the probe support movable along the Z-axis track. One or more motors and controllers may be provided to control the carriages to position the probes very precisely to deliver liquid to or to remove liquid from selected receptacles on the bed below the probe support. Examples of known liquid handlers generally consistent with this description can be found, for example, in U.S. Pat. No. 4,422,151. Additional liquid handler descriptions can be found in U.S. Pat. No. 5,988,236, U.S. Pat. No. 6,240,984, U.S. Pat. No. 6,666,065, and U.S. patent application Ser. No. 20040099334 assigned to the assignee of the present application, each of which is incorporated herein by reference.

Liquid chromatography, including high-pressure liquid chromatography (HPLC), is one example of an application in which automated liquid handlers are used. Liquid chromatography is useful in characterizing a sample through separation of its components by flow through a chromatographic column, followed by detection of the separated components with a flow-through detector. Some HPLC systems include an automated liquid handler to load samples. In these systems, the liquid handler moves the probe to load a sample from a sample container and then injects the sample into an injection port. A metal needle may be attached to the probe to facilitate extraction of the sample from the container and injection of the sample into the injection port.

In operation, one or more controllers may be provided to control the probe or probes of various instruments that provide liquid handling and/or liquid chromatography. The one or more controllers control both the movement and the operation of the probe. Operation of the probe includes tasks such as aspirating a specified amount of solution from a well, dispensing a specified amount of solution to a well, aspirating a specified amount of dilution liquid from a reservoir, rinsing the probe, injecting a specified amount of solution to a well, etc. The controller in practice may be a personal computer, a processor, circuitry embedded on a card or a microchip, or the like. The controller may be integrated with the instrument or physically separate from the instrument. Generally, the controller is a computer that executes an application program to control the probe movement and operation of the instrument or instruments. The application program is an organized list of instructions that, when executed, cause the instrument or instruments to behave in a predetermined manner. Prior controller applications were designed to control a specific device such as a specific liquid handler or liquid chromatography system that may include multiple instruments. As a result, separate application programs were required to interact with each device. What is needed is an application program that is independent of the device such that the same application program can be used to control different devices.

The term "target" refers to instrument components like tubes, vials, spots, or handles. Unlike tubes and vials, handles are positions on a rack that are not designed to hold liquid, but are instead used to provide a way to move a mobile rack using the instrument's probes. Targets are assigned to a zone. A group of targets placed to provide a function such as drain, inject, collect, sink, etc. form a zone. Zones are locations where the instrument moves to perform a particular action. Current devices can assign a target to a single zone. However, current devices do not provide the capability to assign a target to multiple zones. The function of a target may change as an application of the instrument is performed. Thus, what is needed is an application program that can assign a target to multiple zones.

In some instances, users of various devices require a use of the device in a mode that is different from the designed use. Additionally, it is important to test an application developed for a device prior to execution of the application using the device hardware to ensure that the application has been configured correctly. As a result, an application program may include a simulation mode of operation that sequences through the steps of the application identifying hardware limitations and allowing the user to identify errors in the application configuration. However, the typical simulation mode does not allow use of the device hardware in a mode that does not conform with the designed device usage limitations. Thus, what is needed, is an application program that allows the user to execute a simulation mode that permits the device hardware to be used in a mode that does not conform with designed usage.

SUMMARY OF THE INVENTION

An exemplary embodiment of the invention relates to a controller that controls a sequence of actions at a device. The controller includes computer instructions that receive a plurality of user inputs and command information associated with an action for the device to perform. The first user input defines a target in a bed layout of the device. The second user input assigns the target to a first zone of the bed layout. The third user input assigns the target to a second zone of the bed layout. The fourth user input indicates an operational mode for controlling performance of the action. The operational mode includes a non-validation mode defining a state of operation wherein a device limitation is not imposed to restrict the action. The command information includes a command name identifying the action and a device identifier. A unique command method corresponding to the device identifier and to the command name is identified and executed to control operation of the device as it performs the action at the defined target without imposing the device limitation if the fourth user input indicates the non-validation mode.

An exemplary embodiment of the invention relates to a method of controlling an instrument, wherein the instrument supports assignment of a target to a plurality of zones in a bed layout of the instrument. The method includes receiving a first user input that defines a target in a bed layout of a device, wherein the bed layout defines an arrangement of a plurality of potential targets; receiving a second user input that assigns the defined target to a first zone of the bed layout, wherein the first zone identifies a first group of one or more targets of the plurality of potential targets at which to perform a first type of action; receiving a third user input that assigns the defined target to a second zone of the bed layout, wherein the second zone identifies a second group of one or more targets of the plurality of potential targets at which to perform a second type of action; and controlling operation of the device as it performs the first type of action and the second type of action at the defined target Another exemplary embodiment of the invention includes computer-readable instructions that, upon execution by a processor, cause the processor to implement the operations of the method. Yet another exemplary embodiment of the invention includes a controller having computer instructions that implement the operations of the method. Still another exemplary embodiment includes a system that includes the device and the controller.

Another exemplary embodiment of the invention relates to a method of providing device independent controls. The method includes receiving command information associated with an action for a device to perform, wherein the command information includes a command name, and a device identifier; identifying a unique command method corresponding to the device identifier and to the command name; and executing the identified unique command method to control operation of the device as it performs the action. The command name identifies the action and the device identifier identifies the device. The identified unique command method includes instructions to control the action for the device to perform.

Another exemplary embodiment of the invention includes computer-readable instructions that, upon execution by a processor, cause the processor to implement the operations of the method. Yet another exemplary embodiment of the invention includes a controller having computer instructions that implement the operations of the method. Still another exemplary embodiment includes a system that includes the device and the controller.

Another exemplary embodiment of the invention relates to a method of operating a device in an atypical mode of operation. The method includes receiving a first user input that defines an application, wherein execution of the defined application causes a device to perform a sequence of actions; receiving a second user input that indicates an operational mode for executing the defined application, wherein the operational mode includes a non-validation mode, the non-validation mode defining a state of operation of the defined application wherein a device limitation is not imposed to restrict the sequence of actions; and executing the sequence of actions without imposing the device limitation if the second user input indicates the non-validation mode.

Another exemplary embodiment of the invention includes computer-readable instructions that, upon execution by a processor, cause the processor to implement the operations of the method. Yet another exemplary embodiment of the invention includes a controller having computer instructions that implement the operations of the method. Still another exemplary embodiment includes a system that includes the device and the controller.

Other principal features and advantages of the invention will become apparent to those skilled in the art upon review of the following drawings, the detailed description, and the appended claims.

BRIEF DESCRIPTION OF THE DRAWINGS

The preferred embodiments will hereafter be described with reference to the accompanying drawings, wherein like numerals will denote like elements.

FIG. 7 is a first example rack layout.

FIG. 8 is a second example rack layout.

FIG. 8a is an exploded view of the second example rack layout of FIG. 8.

FIG. 9 is a third example rack layout.

FIG. 17 depicts a loop container of the control application of FIG. 4 in an exemplary embodiment.

FIG. 18 depicts a loop properties window of the control application of FIG. 4 in an exemplary embodiment.

FIG. 19 depicts a conditional operator container of the control application of FIG. 4 in an exemplary embodiment.

FIG. 20 depicts a conditional operator properties window of the control application of FIG. 4 in an exemplary embodiment.

FIG. 21 depicts a label container of the control application of FIG. 4 in an exemplary embodiment.

FIG. 22 depicts a Goto-label container of the control application of FIG. 4 in an exemplary embodiment.

FIG. 29 depicts a user interface for defining an application execution of an application using the control application of FIG. 4 in an exemplary embodiment.

FIG. 30 depicts an application execution user interface of the control application of FIG. 4 in an exemplary embodiment.

DETAILED DESCRIPTION OF THE PREFERRED EMBODIMENTS

A liquid handling apparatus may be used as a fraction collector, sampler, dispenser, diluter, injector, etc. A controller utilizes an application program to drive three motors that move a liquid handling probe suitable for dispensing, sampling, etc. in two horizontal directions and in a vertical direction with respect to an array of test tubes or similar receptacles. The apparatus is capable of operating in several modes of dispensing and withdrawal operations, including modes based on the number of drops dispensed or the time spent over each receptacle. The pattern of the movement of the liquid handling tube or dispensing head is selectable to suit the mode of operation of the liquid handling apparatus as well as the type of container and the number of containers being used at a particular time.

Figure 1:
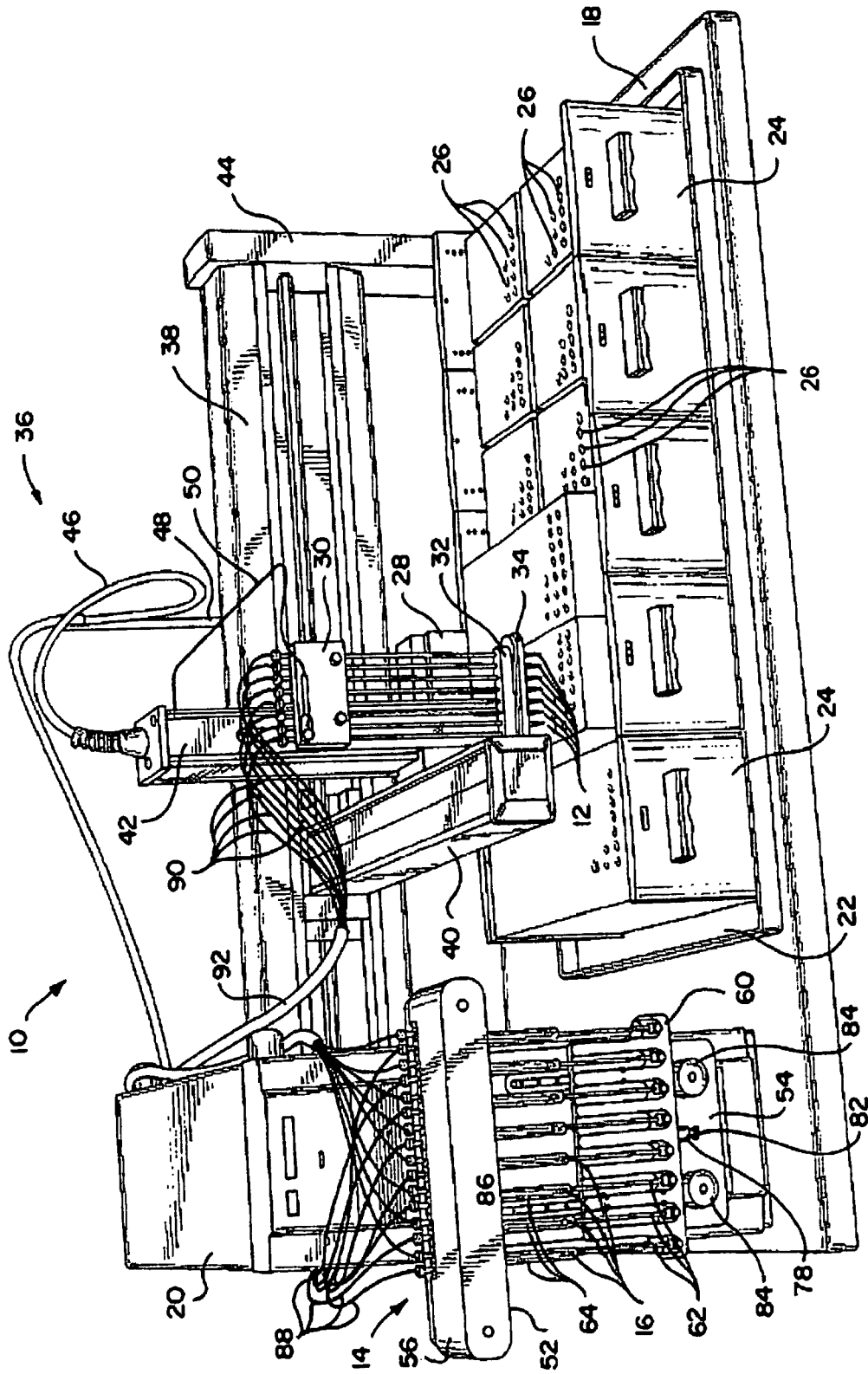
FIG. 1 is a diagram of a liquid handler system.

For exemplification, there is illustrated in FIG. 1 an automated liquid handler designated as a whole by the reference numeral 10. The liquid handler 10 has multiple probes 12 though a single probe 12 may be used. There may be a fewer or a greater number of probes 12 in the liquid handler 10. The liquid handler 10 includes a syringe pump assembly generally designated as 14 that is mounted to a housing 20. The assembly 14 includes a syringe pump 16 corresponding to each of the multiple probes 12. The liquid handler 10 may be part of another system such as a liquid-chromatography system.

The automated liquid handler 10 illustrated in FIG. 1 includes a base 18. The base 18 supports a bed 22 upon which are supported one or more racks 24 that may hold numerous receptacles 26 for containing liquid samples and/or other liquids. The bed 22 accommodates various types and combinations of racks such as racks for supporting vials and vessels and modular reservoirs of different sizes and types, and racks for containing microplates having an array of numerous sample containing wells, such as for example arrays of ninety-six or three hundred eighty-four wells as related previously. In the illustrated embodiment of the automated liquid handler 10, the bed 22 supports racks 24 containing an array of numerous containers 26 having a variety of capacities. Bed 22 may also support a probe rinse station 28, and in some configurations, the bed 22 may support injection ports for high pressure liquid chromatography (HPLC) assemblies. The racks 24 may hold different numbers, arrangements, and size containers 26. There also may be a fewer or a greater number of racks 24 in the liquid handler 10.

Each probe 12 is a hollow tube, and the probes 12 may be fixed together and held for simultaneous movement in a planar array by a probe holder 30. The probes 12 may be arranged in any suitable configuration. The lower ends of the probes 12 are guided by a probe guide 32 carried by a Z drive foot 34. The array of probes 12 is moved relative to the containers 26 supported in racks 24 on bed 22 by a transport system 36 including an X arm 38, a Y arm 40, and a Z arm 42. The transport system 36 locates the probes 12 precisely in a three coordinate system including X, Y, and Z coordinates. The probes 12 can be located above any corresponding liquid container 26 or above the rinse station 28 or HPLC injection ports, and the probes 12 can be raised and lowered relative to the containers 26, rinse station 28, or injection ports. The probes 12 can be further commanded to dispense or to aspirate any amount of liquid.

The X arm 38 is supported in a fixed position extending behind and above the bed 22 between the housing 20 and an end support 44. The Y arm 40 extends forward from the X arm 38 over the bed 22. An X drive motor associated with the X arm 38 moves the Y arm 40 in the X direction along the length of the bed 22. The Z arm 42 is supported by the Y arm 40 and extends vertically in the Z direction. A Y drive motor associated with the Y arm 40 moves the Z arm 42 in the Y direction across the width of the bed 22. The probes 12 in the probe holder 30 are carried by the Z arm 42 and are moved in the vertical Z direction by a Z motor associated with the Z arm 42.

Figure 2:
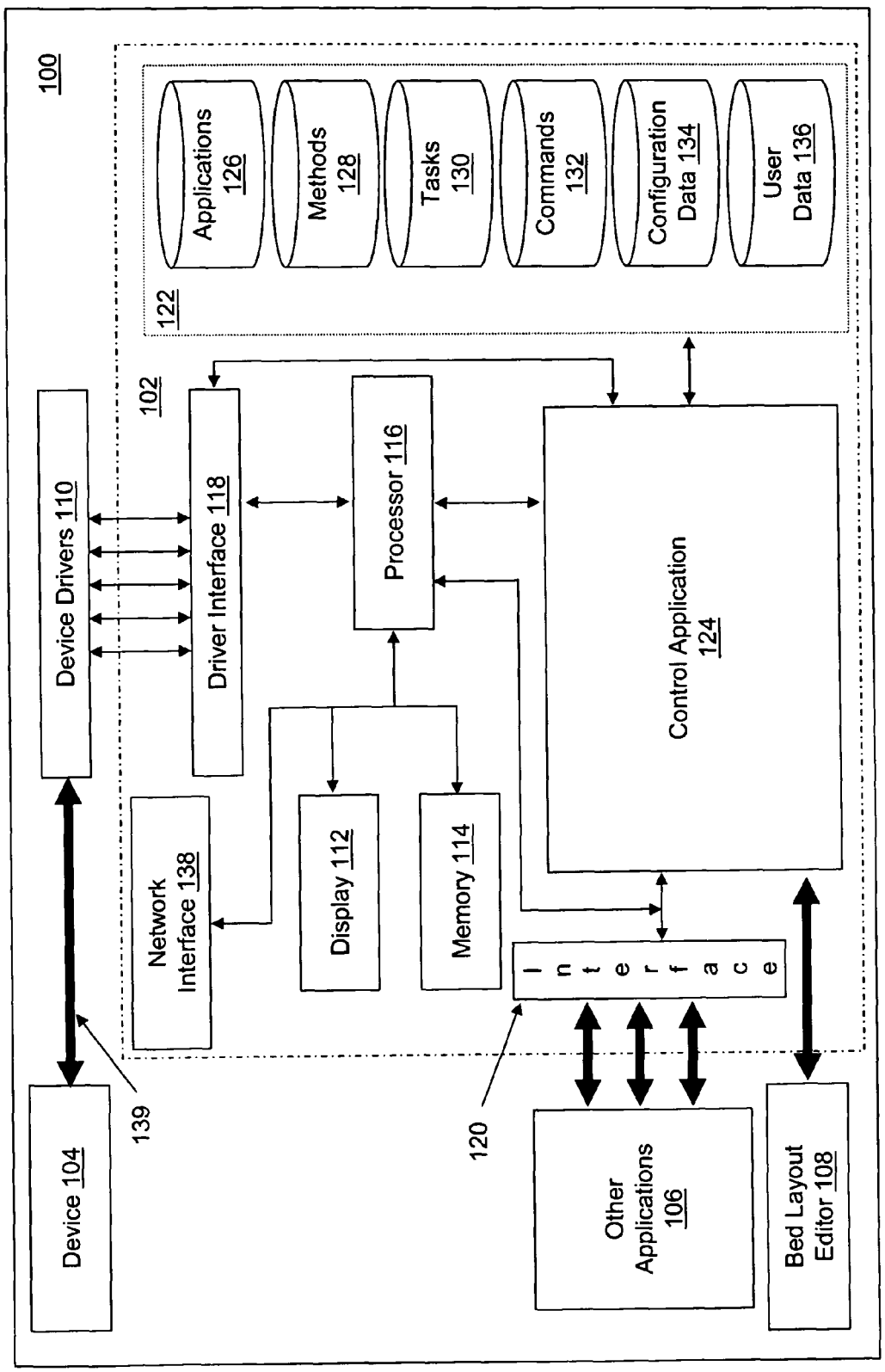
FIG. 2 is a block diagram of a system for controlling a device such as the liquid handler system of FIG. 1 in accordance with an exemplary embodiment.

Liquid handling apparatus 10 is just one example embodiment of a liquid handler design. Other designs may be used. Additionally, a wide variety of other instruments, including, but not limited to, dilutors, pumps, HPLCs, etc. may be used when applying the claimed invention. As such, FIG. 2 shows the instrument or collection of instruments that may comprise an instrumentation apparatus generically as device 104. Device 104 is understood to include any number of different liquid handling device types including those used in liquid chromatography systems.

As shown in FIG. 2, system 100 includes controller 102, the device 104, other applications 106, a bed layout editor 108, and device drivers 110 in an example embodiment. The system 100 may include one or more devices 104 of the same or different types. Thus, the controller 102 may control simultaneously multiple devices 104 of the same or different type. The system 100 may or may not include any other applications 106. The other applications 106 comprise other consumer applications used to control device 104. The controller 102 provides an interface 120 to the other applications 106 so that a single set of commands can be developed to control the device 104 through device drivers 110. Similarly, the system 100 may include a bed layout editor 108 to allow a user to define the layout of the bed of the device 104 to be used in the device application run and to import the bed layout into the controller 102.

The controller 102 includes, a display 112, a memory 114, a processor 116, a driver interface 118, the interface 120 to the other applications 106, a database 122, a control application 124, and a network interface 138 in an exemplary embodiment. The network interface 138 is optional. The controller 102 uses the network interface 138 if the controller 102 requires a connection to the other applications 106, the bed layout editor 108, and/or the device drivers 110 using a network.

The controller 102 controls the operation of the device 104 through the device drivers 110. Because the controller 102 may control different device types, the driver interface 118 of the controller 102 interfaces with multiple device drivers 110 designed to communicate with different device types. The device driver 110 selected by the controller 102 depends on the device type 104 to which the controller 102 interfaces at a specific instant. The device driver 110 acts as a translator between the device 104 and the driver interface 118 of the controller 102. Each device type has a set of specialized controls that its device driver understands and uses to communicate with the device 104. The controls generally are not visible to the user of the controller 102. The appropriate device driver 110 may communicate with the device 104 through communication interface 139. In an example embodiment, the communication interface 139 may be a serial input output communication interface. The controller 102 does not directly control device 104. Instead, the controller 102 issues generic commands through the driver interface 118 to the appropriate device driver 110 that communicates the appropriate control commands to the device 104.

The display 112 may present information to the user of the controller 102 including, but not limited to, information from the control application 124, the bed layout editor 108, the other application 106, etc. The display 112 may be, but is not limited to, a thin film transistor (TFT) display, a light emitting diode (LED) display, a Liquid Crystal Display (LCD), a Cathode Ray Tube (CRT) display, etc.

The memory 114 may be the electronic holding place for an operating system of the controller 102, the other applications 106, the bed layout editor 108, the device drivers 110, the driver interface 118, the interface 120, the control application 124, and/or the database 122 so that the information can be reached quickly by the controller's processor 116. The controller 102 may have a plurality of memories 114 using different memory technologies including, but not limited to, Random Access Memory (RAM), Read Only Memory (ROM), flash memory, and the like. Data in RAM is volatile meaning that it remains only as long as the controller 102 is turned on. When the controller 102 is turned off, RAM loses its data. The values stored in ROM are always there, whether the controller 102 is on or not. For this reason, it is called non-volatile memory. Flash memory is a type of constantly-powered non-volatile memory that can be erased and reprogrammed in units of memory called blocks.

The processor 116 executes instructions that cause the controller 102 to perform various functions. The instructions may be written using one or more programming languages, scripting languages, assembly languages, etc. Additionally, the instructions may be carried out by a special purpose computer, logic circuits, or hardware circuits. Thus, the processor 116 may be implemented in hardware, firmware, software, or any combination of these methods. The term "execution" refers to the process of running an application or program or the carrying out of the operation called for by an instruction. The processor 116 executes an application meaning that it performs the operations called for by that application in the form of a series of instructions. The processor 116 may retrieve an application from a non-volatile memory that is generally some form of ROM or flash memory and may copy the instructions in an executable form to a temporary memory that is generally some form of RAM. The processor 116 may execute instructions embodied, for example, in the driver interface 118, in the interface 120, in the control application 124, etc. The controller 102 may include one or more processors 116.

The driver interface 118, the interface 120, the control application 124, the operating system, the other applications 106, the bed layout editor 108, etc. may be executed by the same processor 116. Alternatively, the driver interface 118, the interface 120, the control application 124, the operating system, the other applications 106, the bed layout editor 108, etc. may be executed by some combination of multiple processors. The driver interface 118, the interface 120, the control application 124, the operating system, the other applications 106, the bed layout editor 108, etc. may be written in the same or different computer languages including, but not limited to high level languages, scripting languages, assembly languages, etc.

A series of controls to the device 104 constitute a command. Control application 124 generates generic commands that the appropriate driver interface 118 translates into specialized commands for the corresponding device driver 110. Device driver 110 translates the specialized commands into a series of controls that are executed by the device 104. The generic commands issued by the control application 124 provide the same calling structure for each distinct command for all device types. For example, MoveTo is a command that moves the probe arm so that the specified probe will be centered on the specified well in the specified zone of the bed. The MoveTo command accepts four parameters: an instrument name, a probe id, a zone name, and a well number regardless of the device type 104. As another example, LLF is a command that moves the specified probe to the new target Z position unless the liquid detector stops the probe first. The LLF command accepts three parameters: an instrument name, a probe id, and a Z movement regardless of the device type 104. Generally, each command performs one specific action and comprises one or more controls.

The database 122 contains data for the control application 124 in an exemplary embodiment. The database 122 may group the data based on the device type. The database 122 may store the control application data for example in groups defined as applications 126, methods 128, tasks 130, commands 132, configuration data 134, and user data 136 as shown in FIG. 2. User data includes information associated with users of the device including a name, a password, a group, etc. Access to the control application 124 may be controlled based on the user data. The data groups may be stored to a single database 122 or to multiple databases that are accessible by the controller 102. When a new device type is added to the system 100, the appropriate applications 126, methods 128, tasks 130, commands 132, configuration data 134, and user data 136 for the device type are added to the database 122. The hierarchical structure of the database 122 mirrors the structure of the control application 124 in that the applications 126 are made up of one or more methods 128. The methods 128 are made up of one or more tasks 130, configuration data 134, and user data 136. The tasks 130 are made up of one or more commands 132. In a preferred embodiment, the database format uses the eXtensible Markup Language (XML) format.

The control application 124 is an organized set of instructions that, when executed, cause the device 104 to behave in a predetermined manner. The control application 124 may be written using one or more programming languages, assembly languages, scripting languages, etc. The term "execution" is the process of carrying out the instructions called for by the control application 124. For the control application 124 to execute, the application may be translated into a machine language that the controller 102 understands. The machine language version of the control application 124 is generally known as the executable and is the commercially available version of the control application 124. The user executes the control application 124 by selecting the control application 124 for launch. Launching the control application 124 generally entails retrieving the executable from a permanent memory device and copying the executable to a temporary memory device, generally some form of RAM. The permanent memory device may be, but is not limited to, a hard disk, a floppy disk, a CD-ROM, etc.

An application stored in the applications 126 is a series of methods that when executed by the control application 124 provide a desired result from the device 104. A method stored in the methods 128 is a series of tasks that represents a group of actions to be executed by the device 104. For example a method "Method1" may include tasks such as aspirate1, dispense1, aspirate2, aspirate3, dispense2, home, etc. A task stored in the tasks 130 is a series of command(s), other task(s), operator(s), variable(s), and/or expression(s) that represent a sequence of related actions to be performed by the device 104. A command stored in the commands 132 is a series of control calls and represents a single action on the device 104. A control call is an actual call on the device 104. The configuration stored in the configuration data 134 defines the group of selected instruments that comprise device 104 and are chosen to be grouped together for the purpose of running the application.

The bed layout defines the arrangement of receptacles on the bed of the device 104. The bed layout is comprised of racks that generally are rectangular trays with a number of wells. The tray is a placeholder with footprints to hold the racks. The well is a place holder for a target. A group of targets placed to provide a function during the application execution, such as drain, inject, collect, sink, etc., form a zone. Targets are assigned to a zone during the application definition or build phase. Zones can span multiple trays. Conversely, a tray may be subdivided into different zones.

Figure 3:
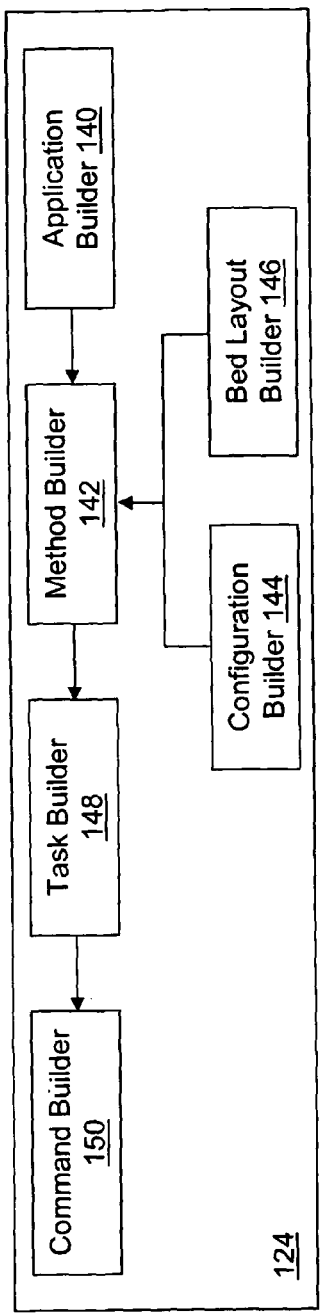
FIG. 3 is a block diagram of a structure for defining controls for the device in accordance with an exemplary embodiment.

As depicted in the example embodiment of FIG. 3, the control application 124 comprises an application builder 140, a method builder 142, a configuration builder 144, a bed layout builder 146, a task builder 148, and a command builder 150 that the user utilizes to define or to build the application for execution by a device 104. The application builder 140, the method builder 142, the configuration builder 144, the bed layout builder 146, the task builder 148, and the command builder 150 act as building blocks to provide for the creation of the command set to be sent to the driver interface 118 thereby causing the device 104 to perform the requested sequence of actions.

Figure 4:
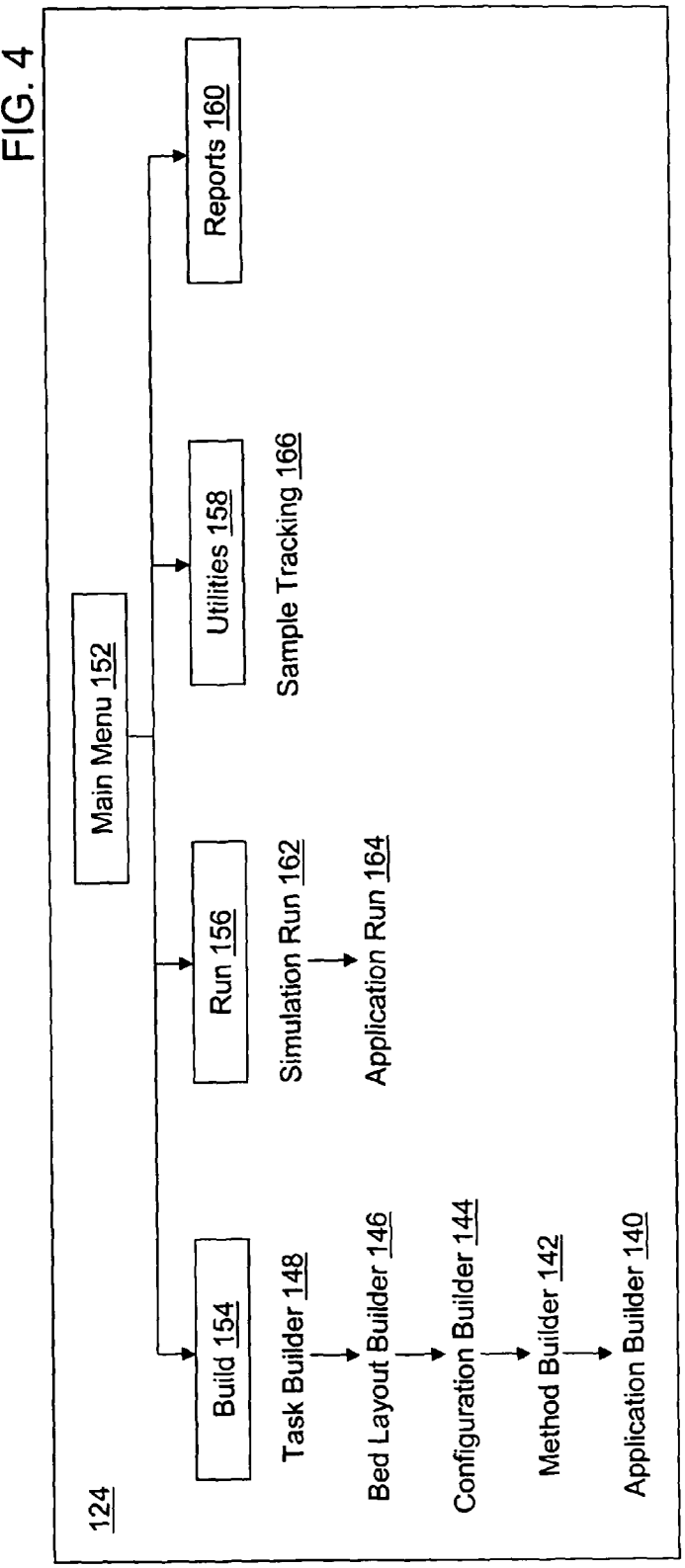
FIG. 4 is an overview block diagram of a control application for controlling the device in accordance with an exemplary embodiment.

As depicted in the example embodiment of FIG. 4, the main menu 152 of the control application 124 includes a build function 154, a run function 156, a utility function 158, and a report function 160. The build function 154 includes the application builder 140, the method builder 142, the configuration builder 144, the bed layout builder 146, and the task builder 148. The application builder 140 allows a user to create and to modify the applications 126. The method builder 142 allows a user to create and to modify the methods 128. The task builder 148 allows a user to create and to modify the tasks 130. The configuration builder 144 allows a user to create and to modify the configuration data 134. The bed layout builder 146 allows a user to work with bed layouts.

The run function 156 includes a simulation run 162 and an application run 164. The simulation run 162 executes a selected application without causing the device 104 to perform the requested actions. The display 112 illustrates the actions that will be performed by the device 104 when the application is run. The application run 164 executes the selected application causing the device 104 to perform the requested actions.

The utility function 158 provides a user with access to additional utility functions including sample tracking 166. For example, the sample tracking 166 provides a graphical representation of which injection produces a given sample and which fraction corresponds to a given peak in a bed layout. Thus, using the sample tracking utility 166 the user can determine the processing history of a specific sample. The report function 160 allows the user to generate and to print reports associated with, for example, the application 126, the application run 164, the simulation run 162, etc.

Figure 5:
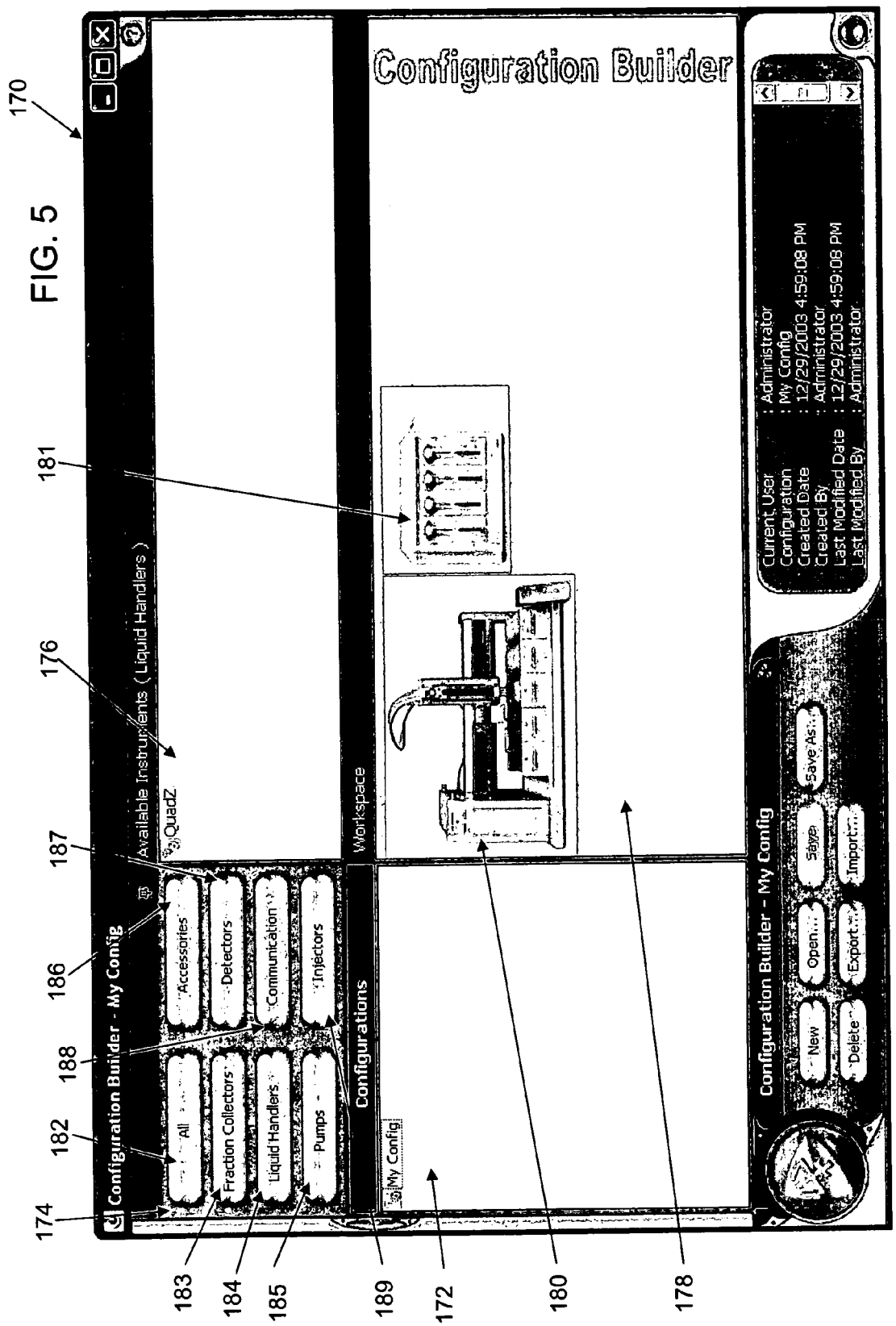
FIG. 5 depicts a user interface for a configuration builder of the control application of FIG. 4 in an exemplary embodiment.

FIG. 5 depicts an example user interface window 170 for the configuration builder 144 in an example embodiment. The configuration builder 144 provides one of the building blocks of the method builder 142. The configuration data 134 provides an identification and a definition of the group of specific instruments that comprise the device 104. The configuration builder 144 user interface window 170 is used to define the configuration that may be stored in the configuration data 134. User interface window 170 includes, but is not limited to, a configuration palette 172, an instrument console 174, an available instruments window 176, and a workspace 178 in an example embodiment. The configuration palette 172 lists the available configuration data 134 defined by the user. The available configuration data 134 was created previously and saved in the database 122 for subsequent use.

The instrument console 174 lists instrument groups to select from in creating or in editing the configuration data 134. Instruments are of different types and are grouped as such as shown in the instrument console 174. Example instrument groups include, but are not limited to, fraction collectors, liquid handlers, pumps, accessories, detectors, communications, and injectors. The instrument types can be selected using instrument group buttons that include, but are not limited to, a fraction collector button 183, a liquid handler button 184, a pump button 185, an accessory button 186, a detector button 187, a communication button 188, and an injector button 189. The available instruments window 176 lists the instruments available for the selected instrument group. The workspace 178 forms the area in which to create or to view a configuration and to view instrument properties. The configuration data 134 may include multiple instruments of the same or of different types.

The configuration builder 144, in an example embodiment, allows a user to create, to modify, to export, to import, to delete, and to view the configuration data 134. A drag-and-drop feature enables easy creation of new configurations. The user can select a configuration to edit, to create, to export, etc. from the configuration palette 172 and can assign a name to the configuration such as "My Config" as shown in FIG. 5. The user can select an instrument group from the instrument console 174. The available instruments of that instrument group are listed in the available instruments window 176. For example, as shown in FIG. 5, the available liquid handlers are the "QuadZ." To view all of the available instruments in the available instruments window 176, a user selects the "All" button 182 from the instrument console 174. The user drags an instrument or instruments from the available instruments window 176 and drops them in the workspace 178. For example, as shown in FIG. 5, the Quad-Z comprises a liquid handler 180 and a quad dilutor 181. Configuration data 134 can be exported from or imported to the control application 124. New configurations are saved in the configuration data 134 of the database 122. Configurations saved in the configuration data 134 are listed in the configuration palette 172 for selection and for possible editing, exporting, deleting, etc. by the user.

Each instrument has a set of properties that may be defined in an instrument properties window in an example embodiment. The properties differ for each type of instrument. The instrument properties window provides a property, a property value, and a property range for each property of that instrument type. For example, the property "InstrumentName" is defined for all instruments. The property value for the property "InstrumentName" may be the name of the instrument. For example, "QuadZ." There may be no property range for the property "InstrumentName." Another example property may be the property "ProbesToUse" that defines the number of probes that can be used with the instrument. The property value may be eight, for example, if the instrument has eight probes. There may be a property range for the property "ProbesToUse" of one to twelve, for example.

Figure 6:
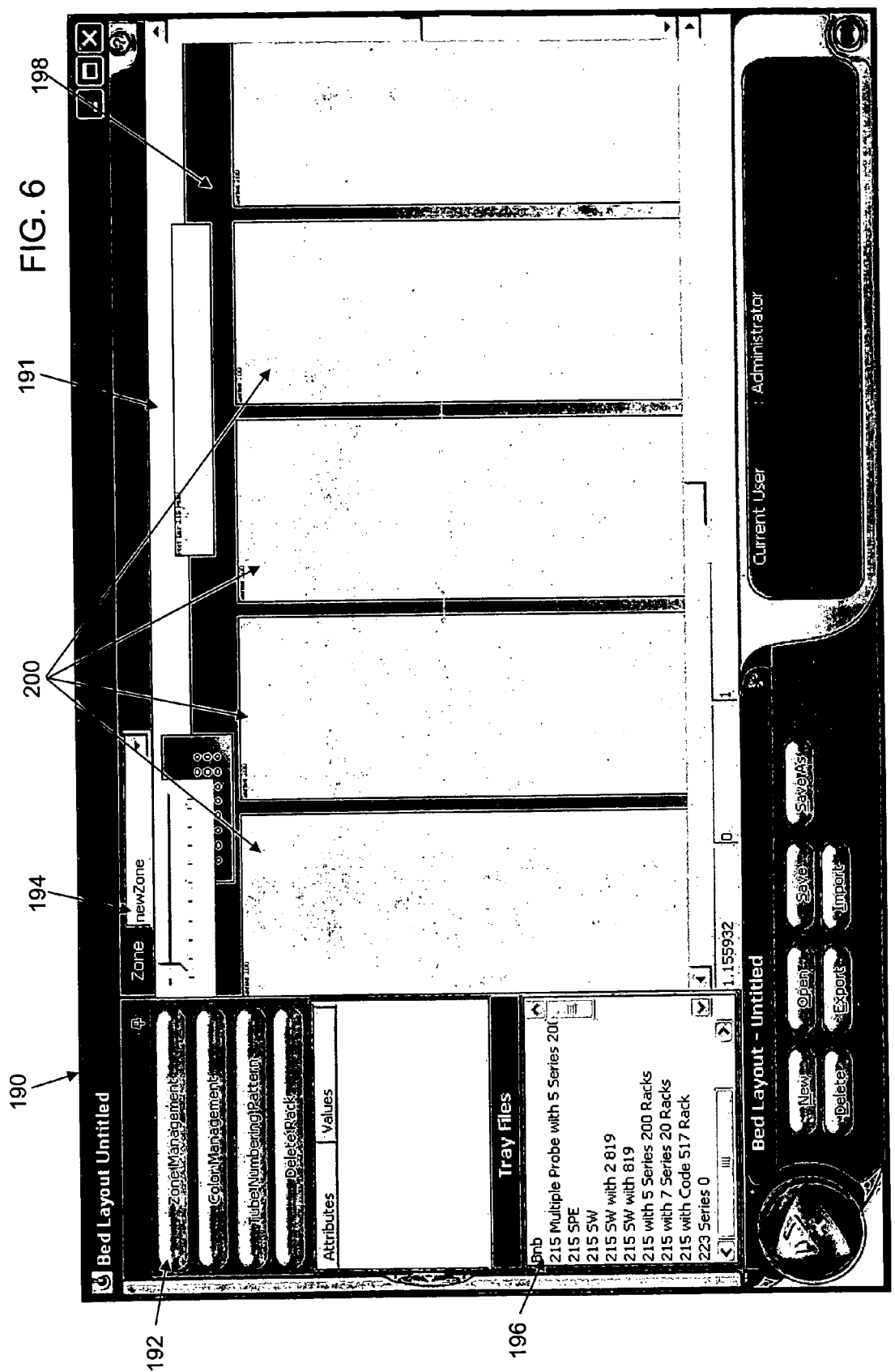
FIG. 6 depicts a user interface for a bed layout builder of the control application of FIG. 4 in an exemplary embodiment.

FIG. 6 depicts an example user interface window 190 for the bed layout builder 146 in an exemplary embodiment. The bed layout builder 146 provides one of the building blocks of the method builder 142. Thus, a bed layout is associated with a method of the application. The bed layout builder 146 allows the user to create, to modify, to export, to import, to delete, and to view the bed layout. Example user interface window 190 allows the user to create a new bed layout and provides a visual representation of the bed layout for an instrument. Targets are placed on the bed layout. Each target has a set of properties. For example, targets generally include, but are not limited to an X-Y-Z position and a height. The X-Y-Z position refers to an origin that is defined on the rack that the target is placed on within the bed layout. As the method defined within the application executes, the target location may change. The control application 124 provides for tracking of the target during the application execution as the target moves from zone to zone.

The bed layout builder 146 includes, but is not limited to, a template, one or more footprints, one or more racks, and one or more wells. The template provides a structural pattern for a bed layout and is used as a starting point for creating the bed layout. Thus, a template is essentially a preformed bed layout. Footprints are locations where a rack can be placed within the bed layout. Each rack is compatible with a set of footprints. Some racks may need several footprints to be placed. Footprints also are used to designate locations for one or more rinse station and/or injection port. A footprint may also include a type of rinse station at each rinse station location.

In an example embodiment, the user interface window 190 includes, but is not limited to, a bed layout workspace 191, a zone management button 192, a "Zone" drop-down menu 194, and a template selection menu 196 as shown in FIG. 6. In creating the bed layout, the user selects a template from the template selection menu 196. The user may select a footprint from a provided list based on the selected template. The user interface window 190 refreshes to graphically display the selected template 198 in the bed layout workspace 191. For example, in FIG. 6, an example template comprising five footprints 200 for placing racks is shown. The user can add suitable racks to the footprints 200. For example, FIG. 7 shows a first example bed layout comprised of a first rack 201 and a second rack 202 placed on two different footprints 200. Both racks 201 and 202 contain ninety-six wells for tubes or vials. Rack 201 is arranged in an array of six offset columns and sixteen rows. Rack 202 uses half the area of rack 201 and is arranged in an array of eight columns and twelve rows.

FIG. 8 shows a second example bed layout comprised of a third rack 203 and a fourth rack 204. The ninety-six wells of rack 203 are filled with ninety-six tubes. Of the ninety-six wells of rack 204, only sixteen wells contain tubes. FIG. 8a shows an enlargement of the third rack 203 and the fourth rack 204 in the first footprint 200 of the bed layout. In defining the bed layout, the user may delete the third rack 203 and replace it on the footprint with a fifth rack 205 as shown in FIG. 9. The fifth rack 205 contains three hundred eighty-four wells filled with tubes. Rack 205 is arranged in an array of sixteen columns and twenty-four rows.

Figure 10:
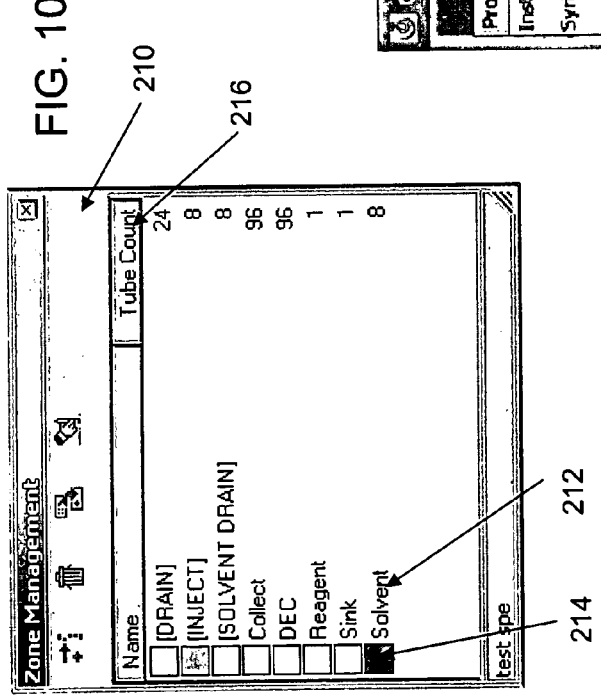
FIG. 10 depicts a user interface for a zone management summary display of the control application of FIG. 4 in an exemplary embodiment.

Selecting the zone management button 192 causes the display of a user interface window that allows the user to create, to modify, or to delete zones. For example, a zone management user interface window 210, shown in FIG. 10, displays information concerning the currently defined zones for the bed layout. New zones can be added and assigned a color for visualization of the zones on the bed layout. The user of the control application 124 allocates each target to one or more zones. As related previously, the user has complete flexibility in assigning targets to zones that may span multiple racks, plates, or instruments. Additionally, each plate or rack may be subdivided into different zones. Additionally, each target can be assigned to multiple zones. The control application 124 provides for tracking of the target across multiple zones as the application run progresses.

The zone management user interface window 210 shows the function of each defined zone 212, the color code 214 used to indicate the location of the zone on the bed layout, and the number of tubes 216 currently assigned to each zone. In creating a new zone, the user defines a unique name (typically identifying the zone function) for the zone, selects the color to indicate the zone tube locations, and selects a starting number for counting the tubes in the zone. The created zone preferably is added to the zone management user interface window 210. The created zone is added to the "zone" drop-down menu 194 shown in FIG. 6 in a preferred embodiment. The user may assign targets to a zone in groups, by rack, individually, etc. For example, the target may be selected from the template 198 by individually "clicking" on each target or by "lassoing" a group of targets by clicking and simultaneously dragging, for example, a pointer across the desired group of targets.

A sample list provides a set of initial values to an application run and is associated with an application during the initialization of the application run process. The sample list may be used when an application process has been initiated using a different control application or controller that is to be continued using the controller 102 and the control application 124. The sample list defines the number of samples to process and initializes variables in each task/method that have not been pre-defined. For example, a sample location, a volume to aspirate or dispense, or conditions such as a flow rate can be defined using the sample list. The sample list also defines type information such as sample description, sample name, or note fields for each sample. Thus, the sample list provides initial parameters for the application run.

Figure 11:
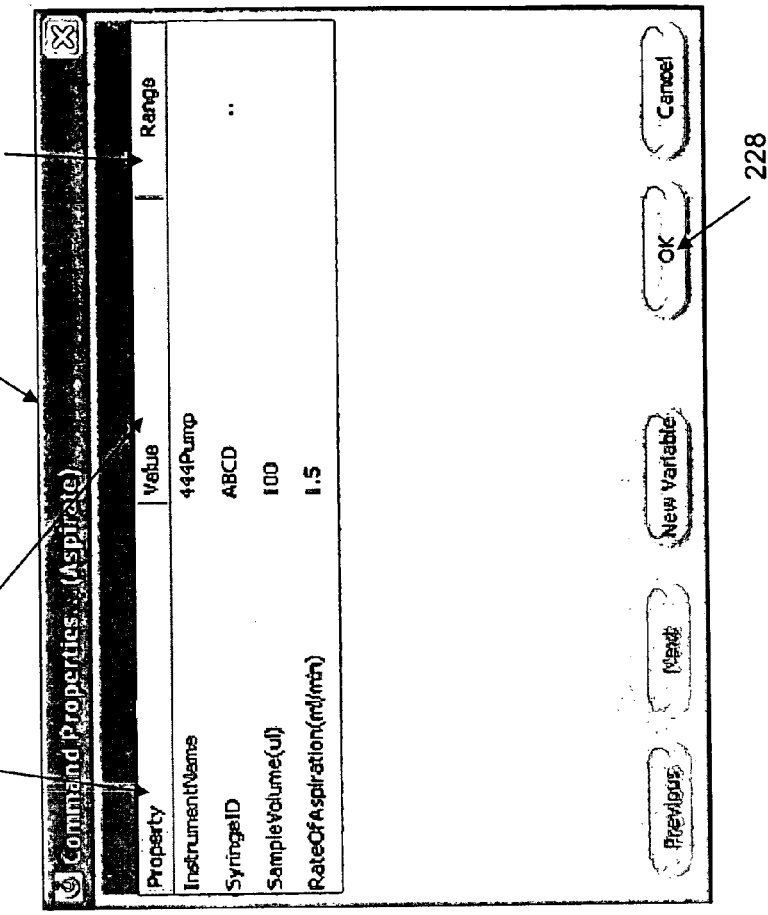
FIG. 11 depicts a user interface for a command properties window of the control application of FIG. 4 in an exemplary embodiment.

The lowest level building block of the control application 124 is the command. The command serves as the building block of the task. The command includes instructions that control the operations of an instrument. Each command has a set of properties associated with its definition. The properties may vary based on the command selected by the user. The command builder 150 provides a user interface that allows the user to define the properties for the command when the command is selected as part of a task. For example, FIG. 11 shows a set of properties for an "Aspirate" command in an exemplary embodiment. The command properties window 220 includes a property name 222, a property value 224, and a property range 226 for each property of the "Aspirate" command. The property name 222 provides a descriptive identifier for the property. The property value 226 specifies the value of the property. The property range 226 may be used to define a minimum and a maximum value for the property. No range specification is necessary. Thus, the user makes the command unique through definition of the property values. For example, a second "Aspirate" command might have a sample volume of 1.5 ml.

Figure 12:
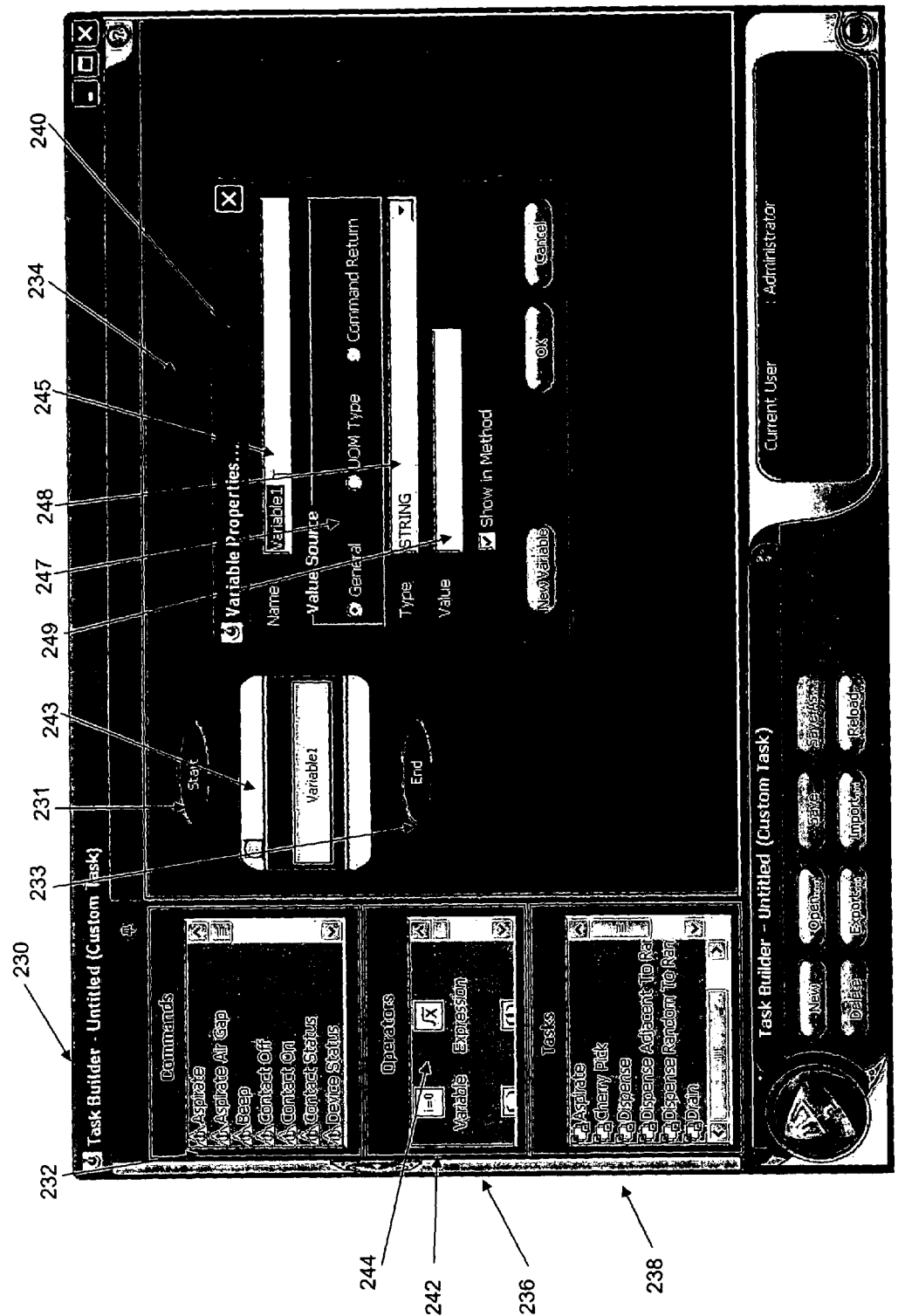
FIG. 12 depicts a user interface for a task builder of the control application of FIG. 4 in an exemplary embodiment.

With reference to the example embodiment shown in FIG. 12, a user defines a new command by dragging a similar command from a command palette 232 of a user interface window 230 of the task builder 148 and dropping it in a task builder workspace 234 between a start indicator 231 and a stop indicator 233. The command palette 232 displays a list of the commands contained in the commands 132 stored in the database 122. The appropriate command property window 220 of the selected similar command is displayed. The user defines the property values appropriately for the new command and selects the "OK" button 228 as shown in FIG. 11. The new command appears on the task builder workspace 234.

In an example embodiment, the user interface window 230 of the task builder 148 includes, but is not limited to, the command palette 232, the task builder workspace 234, an operators palette 236, and a task palette 238. The task builder 148 allows the user to create, to modify, to delete, to export, and to import tasks. The task is the building block for a method. The user creates the task by dragging a task component that may include, but is not limited to, a command, an operator, and/or a task from the respective palette to the task builder workspace 234 between the start indicator 231 and the stop indicator 233. The user may place any number of task components on the task builder workspace 234 when creating the task. Thus, a user can create simple tasks consisting of a single command, operator, or task. Alternatively, the user can create complex tasks comprised of a number of commands, operators, and/or tasks. The user places the task components on the task builder workspace 234 in the order that the task components should execute. Saved tasks are listed in the task palette 238 and saved to the tasks 130 of the database 122 in an exemplary embodiment. Multiple user interface windows 230 of the task builder 148 may be open at the same time.

Figure 16:
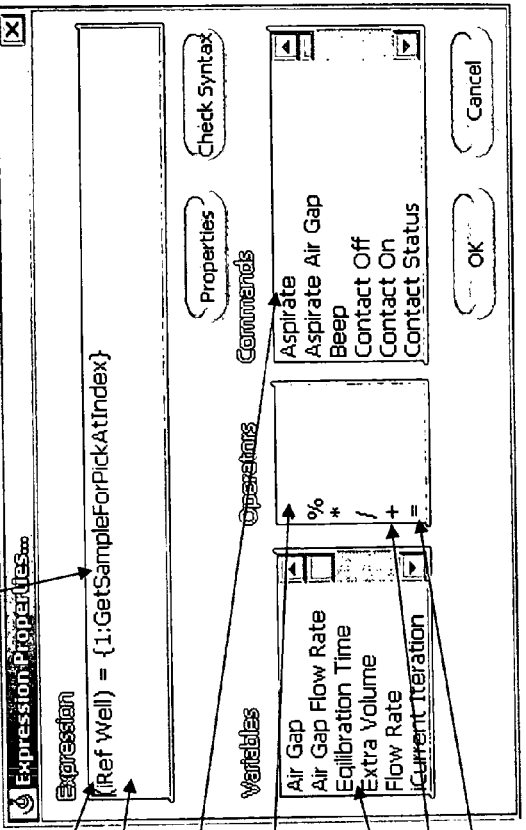
FIG. 16 depicts an operator's palette of the control application of FIG. 4 in an exemplary embodiment.

As shown in FIG. 16 in an expanded view, the operators palette 236 includes, but is not limited to, a variable 242, an expression 244, a loop operator 261, a If . . . EndIf" operator 269, an "If . . . Else" operator 273, a label operator 286, and a "Goto" operator 287. When selected and dragged to the task builder workspace 234, the variable 242 allows the user to create a named container that accepts values for properties that may be specified for a task, for a method, or derived from a sample list. The user drags the variable 242 and drops it in the task builder workspace 234 within the task between the start indicator 231 and the stop indicator 233. The variable 242 may be listed at the beginning of the task. In an exemplary embodiment, the variable 242 can be used in a command, in a loop, in an expression, in a conditional operator, in an unconditional operator, and/or in a task.

For example, as shown in FIG. 12, the variable 242 dragged to the task builder workspace 234 causes the variable container 243 to be added to the task builder workspace 234 between the start indicator 231 and the stop indicator 233 and opens the variable properties window 240. The user defines the variable using the parameters presented in the variable properties window 240. In an exemplary embodiment, the parameters defining a variable may include, but are not limited to, a property name window 245, a value source radio button 247, a variable type drop-down list 248, and a variable value 249. The user may define the name of the variable in the property name window 245. In an exemplary embodiment, the name of the variable is used to name the variable in the variable container 243 and to reference the variable in a variable list selectable for a command, a loop, an expression, a conditional operator, an unconditional operator, and/or a task. The variable value 249 defines the value of the variable. The format (i.e. number, string, etc.) of the value entered in the variable value 249 depends on the value source radio button 247 selection and the variable type drop-down list 248 selection.

Figure 13:
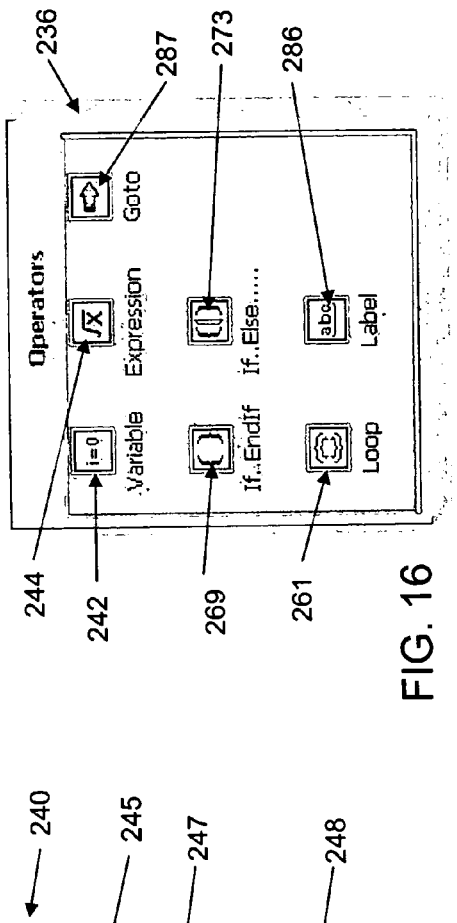
FIG. 13 depicts a user interface for a variable properties window of the control application of FIG. 4 in an exemplary embodiment.

The user selects the value source using the value source radio buttons 247 in an exemplary embodiment. The value source may be general, unit of measure (UOM) type, or command return. The general value source can be selected to create a variable having a numeric or string value. The UOM type value source can be selected to create a variable having units of movement. The command return value source can be selected to create a variable to store return values of commands. The user selects the variable type from the variable type drop-down list 248. In an exemplary embodiment, the selections included in the variable type drop-down list 248 depend on the value source radio button 247 selected for the variable. For a general value source type variable, the selections may include, but are not limited to, a number, a string, a true/false value, a well, a zone, an instrument, and a "z" value as shown in the example embodiment of FIG. 13. The well type means the variable provides a well number. The zone type means the variable provides a zone name. The instrument type means the variable provides an instrument name. The "z value" type means the variable provides "option" property values for the "MoveZ" command. In an exemplary embodiment for a UOM type variable, the selections may include, but are not limited to, a XYZ Movement, a speed of movement, a volume, a flow rate, and a time. The XYZ Movement type means the variable specifies the distance value for the X, Y-axis, Z-arm, and/or probe spacing commands. The speed of movement type means the variable specifies the value for the speed of the z-arm. The volume type means the variable specifies the sample volume for an aspirate or a dispense command. The flow rate type means the variable specifies the rate of flow for an aspirate or a dispense command. The time type means the variable specifies the time for a beep or for a timer command. In an exemplary embodiment for a command return type variable, the selections may include, but are not limited to, success/fail, true/false/fail, on/off/fail, OK/continue/abort, number/fail, instrument status, and/or string/fail.

Figure 14:
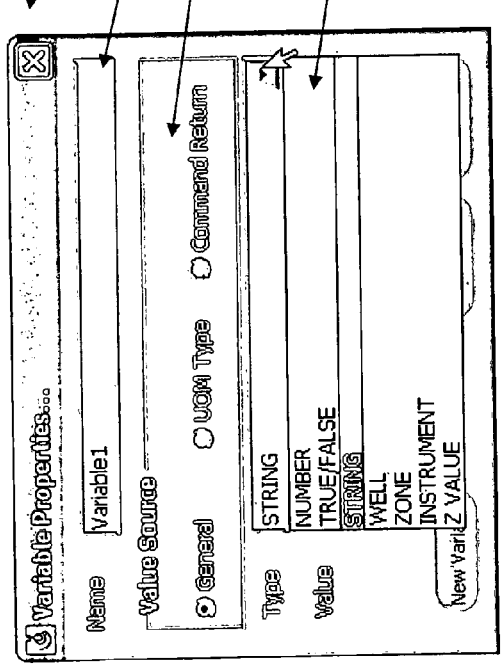
FIG. 14 depicts an expression container of the control application of FIG. 4 in an exemplary embodiment.
Figure 15:
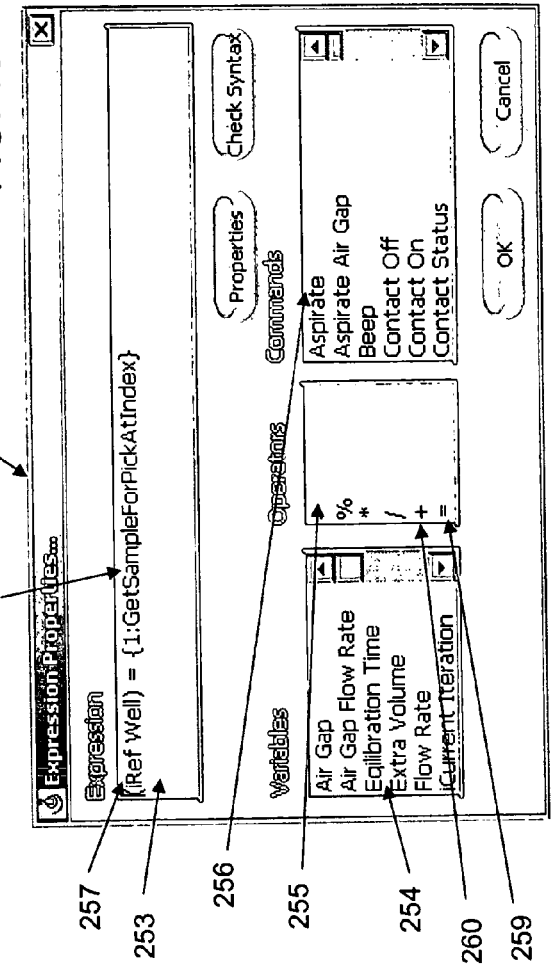
FIG. 15 depicts an expression properties window of the control application of FIG. 4 in an exemplary embodiment.

When selected and dragged to the task builder workspace 234, the expression 244 allows the user to create a statement used to perform calculations and to derive a result. The user drags the expression 244 and drops it in the task builder workspace 234 at the appropriate location within the task between the start indicator 231 and the stop indicator 233. The expression may include, but is not limited to, a constant, a variable, and/or a command that are separated by operators. In an exemplary embodiment, an expression container 250, shown in FIG. 14, opens in the task builder workspace 234 between the start indicator 231 and the stop indicator 233, and an "Expression Properties" window 252, as shown in FIG. 15, is displayed in the task builder workspace 234.

In an exemplary embodiment, the "Expression Properties" window 252 may include, but is not limited to, an expression window 253, a variable list 254, an operator selection list 255, and a command list 256. An expression has a left hand side 257 left of an assignment operator 259 and a right hand side 258 right of the assignment operator 259. The left hand side 257 is populated by selecting a variable from the variable list 254. The right hand side 258 is populated by selecting a variable from the variable list 254, a command from the command list 256, and/or by typing a constant into the expression window 253. Compound expressions can be created by selecting any number of additional variables and/or commands and/or by typing any number of constants each separated by an operator from the operator selection list 255. For example, the expression X=Y+10.46 is created by selecting "X" as a variable from the variable list 254, selecting the assignment operator 259, selecting "Y" as a variable from the variable list 254, selecting an addition operator 260, and typing the number "10.46" in the expression window.

When selected and dragged to the task builder workspace 234, the loop operator 261 allows the user to create a repetition of actions or statements contained within the created loop. The user drags the loop operator 261 and drops it in the task builder workspace 234 at the appropriate location within the task between the start indicator 231 and the stop indicator 233. In an exemplary embodiment, a loop container 262, shown in FIG. 17, opens in the task builder workspace 234 between the start indicator 231 and the stop indicator 233, and a "Loop Properties" window 265 is displayed in the task builder workspace 234 as shown in FIG. 18. A name property window 266 allows the user to define the loop name that appears as the title of the loop. A loop count property window 267 allows the user to specify the number of times the loop is repeated. The loop count property may be a variable so that the number of repetitions of the loop is not fixed at the beginning of the application run. A loop operator 261 can be positioned anywhere in the task builder workspace 234 depending on the location that the user drops the loop operator 261. After defining the loop properties, the user selects the "OK" button 268 and the loop definition is saved. Tasks, commands, conditional operators, unconditional operators, and/or expressions can be added inside the loop container 262 between the upper bar 263 and the lower bar 264. The upper bar 263 of the loop container 262 depicts the beginning of the loop. The lower bar 264 of the loop container 262 depicts the end of the loop. A loop can be created within an existing loop to create a nested loop.

In an exemplary embodiment, conditional operators may include, but are not limited to, the "If . . . EndIf" operator 269 and the "If . . . Else" operator 273. Use of the conditional operator allows the user to perform a set of actions only if the defined condition is satisfied. Adding an "else" clause provides for an alternative action if the defined condition is not satisfied. The user drags, for example, the conditional operator 269 and drops it in the task builder workspace 234 at the appropriate location within the task between the start indicator 231 and the stop indicator 233. In an exemplary embodiment, a conditional operator container 270, shown in FIG. 19, opens in the task builder workspace 234 between the start indicator 231 and the stop indicator 233, and a properties window 274 is displayed in the task builder workspace 234 as shown in FIG. 20.

In an exemplary embodiment, the properties window 274 may include, but is not limited to, an expression window 275, a variable list 276, an operator selection list 277, and a command return value list 278. An expression has a left hand side 280 left of a conditional operator and a right hand side 281 right of the conditional operator. Example conditional operators include, but are not limited to, "!=", "==", "<", ">", "<=", and ">=". The left hand side 280 is populated by selecting a variable from the variable list 276. The right hand side 281 is populated by selecting a variable from the variable list 276, a command return value from the command return value list 278, and/or typing a constant in the expression window 275. Compound expressions can be created by selecting any number of additional variables and/or command return values and/or by typing any number of constants each separated by an operator from the operator selection list 277. For example, the conditional expression X<Y+10.46 is created by selecting "X" as a variable from the variable list 276, selecting the less than conditional operator from the operator selection list 277, selecting "Y" as a variable from the variable list 276, selecting an addition operator 280 from the operator selection list 277, and typing the number "10.46" in the expression window 275.

The conditional operator 269, 273 can be positioned anywhere in the task builder workspace 234 between the start indicator 231 and the stop indicator 233 depending on the location that the user drops the conditional operator. After defining the properties, the user selects the "OK" button 279 and the conditional operator definition is saved. Tasks, commands, expressions, Goto-Label operators, and/or loops can be added inside the conditional operator container 270 between the upper bar 271 and the lower bar 272. The upper bar 271 of the conditional operator container 270 depicts the beginning of the conditional operator. The lower bar 272 of the conditional operator container 270 depicts the end of the conditional operator. The actions within the upper bar 271 and the lower bar 272 are performed only if the expression defined in the expression window 275 is true. A conditional operator 269, 273 also can be created within an existing conditional operator to create a nested conditional function.

In an exemplary embodiment, branching operators may include, but are not limited to the label operator 286 and the "Goto" operator 287. Use of the branching operators allows the user to define a task location to which task execution branches when a "Goto" container is reached during the task execution. From the operators palette 236, the user drags the label operator 286 and drops it in the task builder workspace 234 at the point to which the task branches. In an exemplary embodiment, a label container 282, as shown in FIG. 21, opens. The user may define a name for the label container 282 that is displayed in a label field 283. From the operators palette 236, the user drags the "Goto" operator 287 and drops it in the task builder workspace 234 at the point at which the task branches during the task execution. In an exemplary embodiment, a "Goto" container 284, shown in FIG. 22, opens. The user may define a name for the "Goto" container 284 that is displayed in a "Goto" label field 285. The branching operator 286, 287 can be positioned anywhere in the task builder workspace 234 between the start indicator 231 and the stop indicator 233. For example, the task definition below causes the task execution to branch to the "Skip" execution line when the "Goto Skip" execution line is reached. The effect is that, if the syringe volume is greater than or equal to the maximum volume, the aspiration process stops.

Loop
   Syringe Vol=Air Vol+Sample Vol (Expression)
   If Syringe Vol>=Max Vol (Conditional Expression)
     Goto Skip (Goto operator)
   EndIf
   Aspirate Air Gap (Command)
   Aspirate (Task)
End Loop
Skip (Label)

Figure 23:
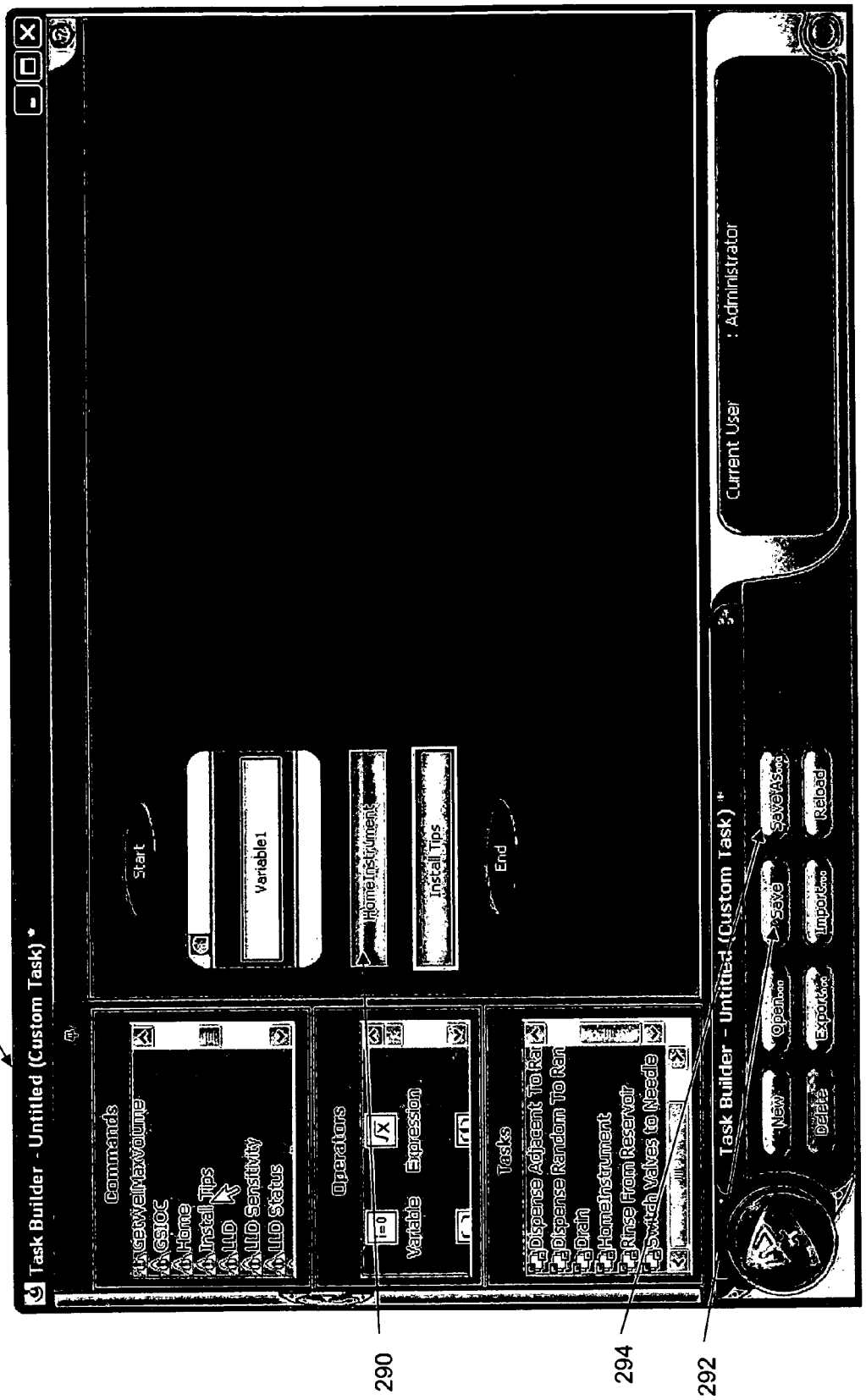
FIG. 23 depicts a task builder of the control application of FIG. 4 in an exemplary embodiment showing a simple task.

The user may create a nested task by including another task within the task. From the task palette 238, the user drags the task and drops it in the task builder workspace 234 between the start indicator 231 and the stop indicator 233 at the appropriate task execution point. For example, as shown in FIG. 23, the "HomeInstrument" task 290 is nested within the example task. In an exemplary embodiment, after a user selects the "Save" button 292 or the "Save As" button 294, the created task is added to the task palette 238 for selection in other tasks and methods. The task is also added to the tasks 130.

Figure 24:
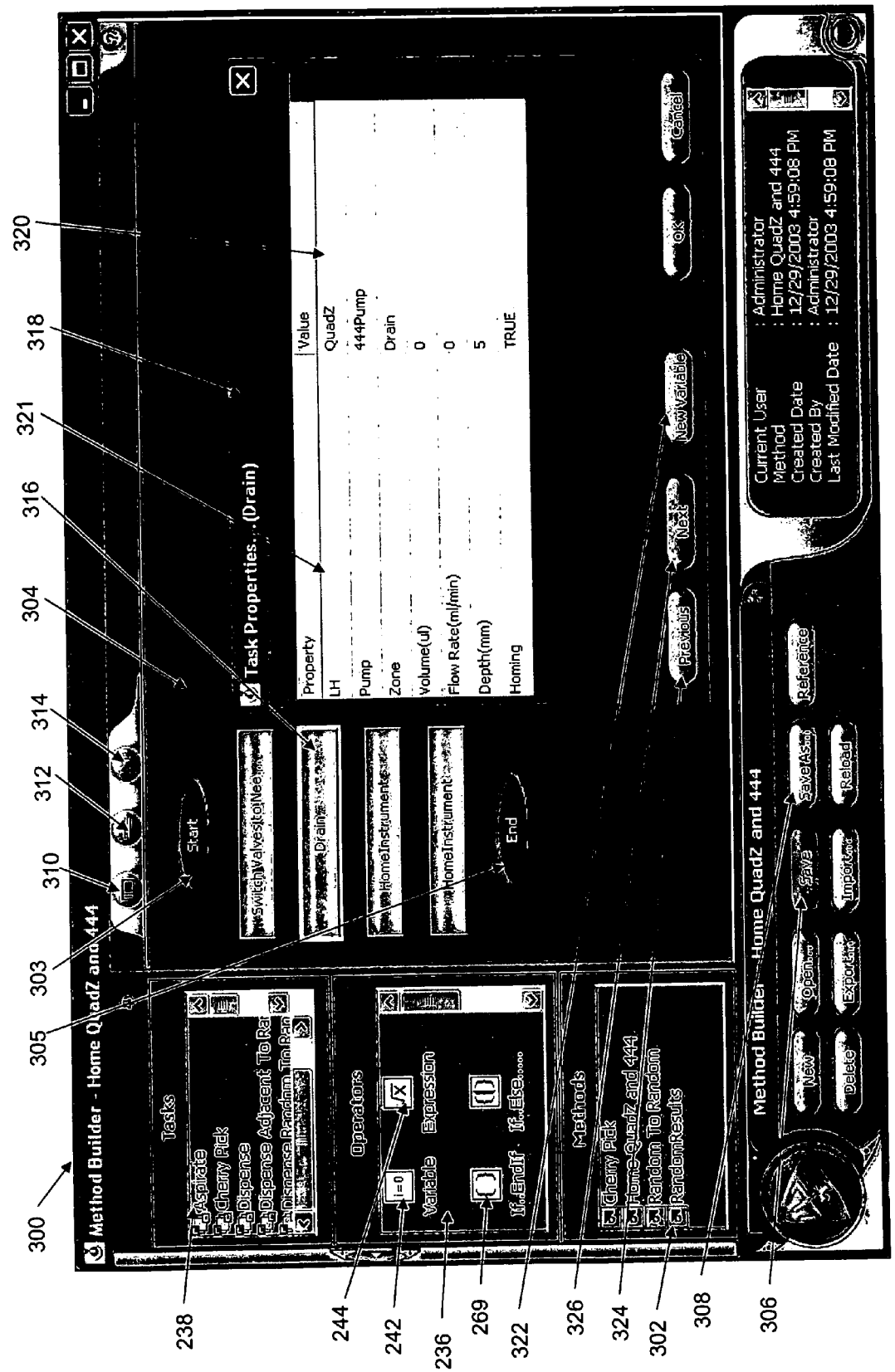
FIG. 24 depicts a method builder of the control application of FIG. 4 in an exemplary embodiment.

In an exemplary embodiment shown in FIG. 24, the user interface window 300 of the method builder 142 includes, but is not limited to, the task palette 238, the operators palette 236, a method palette 302, and a method builder workspace 304. The method builder 142 allows the user to create, to modify, to delete, to export, and to import methods. The method builder 142 user interface window 300 is used to define the method that may be stored in the methods 128. The user creates the method by dragging a task, an operator, or a method from the respective palette to the method builder workspace 304. The user may place any number of tasks, operators, and/or methods on the method builder workspace 304 in creating the method. The user places the tasks, operators, and methods on the method builder workspace 304 in the order that the method elements should execute. Saved methods are listed in the method palette 302 in an exemplary embodiment and are stored in the methods 128. Multiple user interface windows 300 of the method builder 142 can be open at the same time.

The method also may include the configuration and the bed layout. In creating a new method, the user selects the configuration and the bed layout to associate with the method. In an exemplary embodiment, the builder tab 310 of the user interface window 300 of the method builder 142 allows the user to view the method details. In an exemplary embodiment, the bed layout settings tab 312 allows the user to view the bed layout details. In an exemplary embodiment, the configuration settings tab 314 of the user interface window 300 of the method builder 142 allows the user to view the configuration details.

In creating a method, the user may drag a task from the task palette 238 and drop the task in the method builder workspace 304 at the appropriate location within the method. The task icon 316 is positioned at the appropriate location between a start indicator 303 and a stop indicator 305, and the task properties window 318 is displayed in the method builder workspace 304. In an exemplary embodiment, the task properties window 318 allows the user to provide values for the task variables in the property value field 320 of each task property 321. The task properties window 318 also may allow the user to create new variables using the new variable button 322. The task properties window 318 also may allow the user to view the properties of the previous task using the previous button 324 and of the next task using the next button 326, if any.

In creating a method, the user may drag an operator from the operator palette 236 and drop the operator in the method builder workspace 304 at the appropriate location within the method as related previously relative to the task builder workspace 234.

The user may create a nested method by including another method within the method. From the method palette 302, the user drags the method and drops it in the method builder workspace 304 at the appropriate location between the start indicator 303 and the stop indicator 305. In an exemplary embodiment, after a user selects the "Save" button 306 or the "Save As" button 308, the created method is added to the method palette 302 for selection in other methods and in applications. The method is also added to the methods 128.

Figure 25:
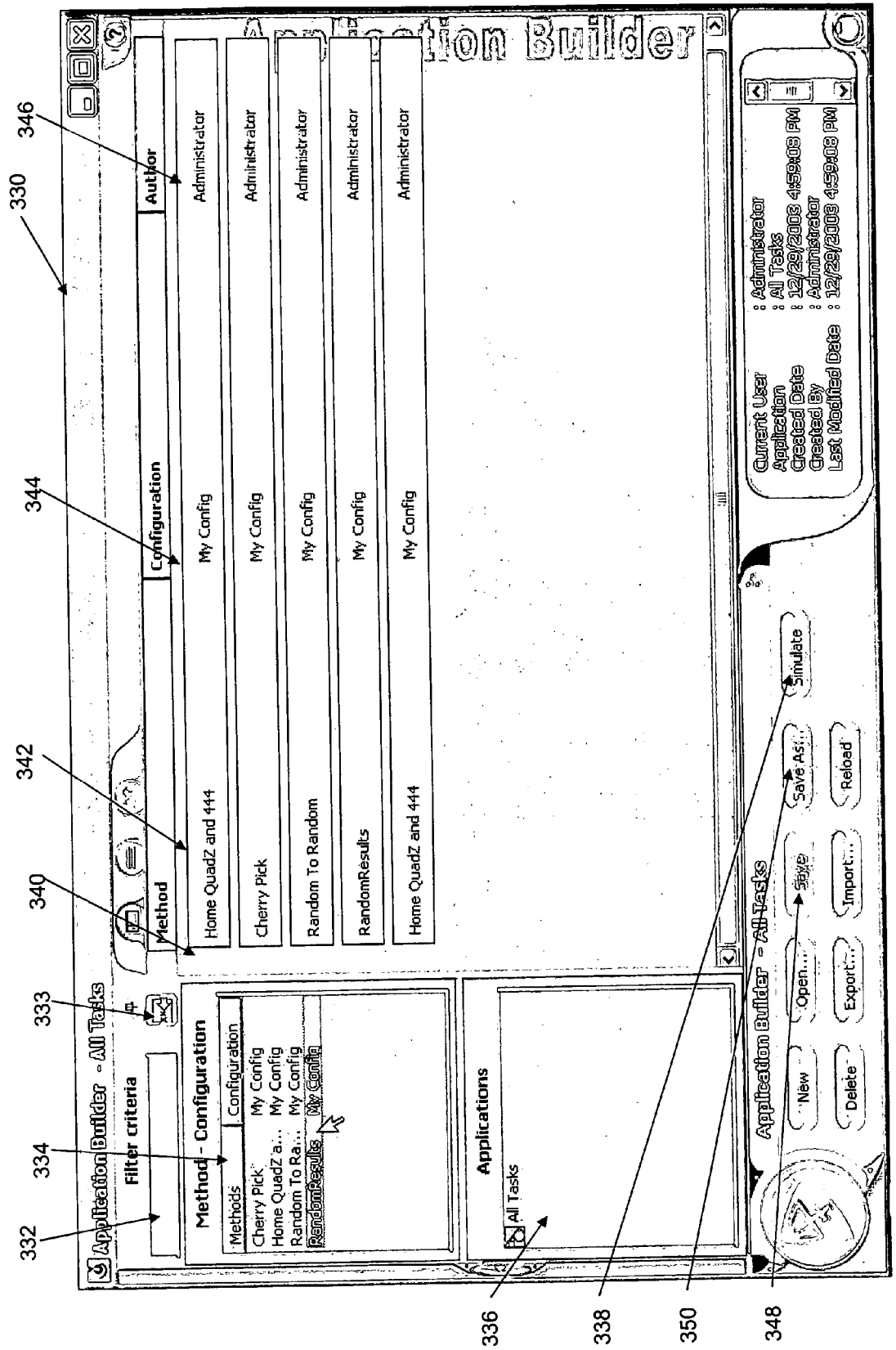
FIG. 25 depicts an application builder of the control application of FIG. 4 in an exemplary embodiment.

As described above, the application comprises one or more methods. The application performs the actions defined in the one or more methods on the instruments specified in the respective configuration defined for each method. The application builder 140 allows the user to create, to view, to modify, to delete, to export, and to import applications and to simulate an application run. In an exemplary embodiment shown in FIG. 25, the user interface window 330 of the application builder 140 includes a filter criteria window 332, a method-configuration palette 334, an application palette 336, a simulate button 338, and an application builder workspace 340. The filter criteria window 332 allows the user to define search criteria. The user may define text that is contained within the methods and the configurations as the search criteria in an exemplary embodiment. After selecting a search button 333, the control application 124 searches the application methods and the configurations and displays the methods and the configurations found in the application based on the search text defined in the filter criteria window 332. The application palette 336 lists the applications created and saved in the applications 126. The user may select an application from the application palette 336 to view, to simulate, to run, to edit, etc. The method-configuration palette 334 lists all of the methods with their respective associated configuration contained in the methods 128. The simulate button 338 allows the user to view an application run without moving the instruments to test the application execution before using the instruments to visually verify that the method is correctly programmed.

Figure 26:
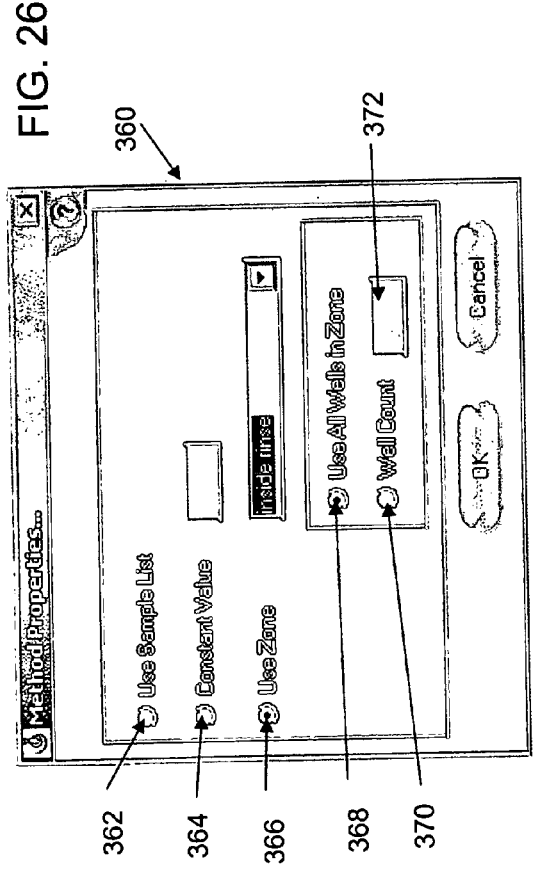
FIG. 26 depicts a method properties window of the control application of FIG. 4 in an exemplary embodiment.

The user creates the application by dragging a method from the method-configuration palette 334 to the application builder workspace 340 and by dropping the method in the application builder workspace 340 at the appropriate location. In an exemplary embodiment, a method name 342, an associated configuration 344, and a name of the author that created the method 346 is displayed in the application builder workspace 340, and a "Method Properties" window 360 (shown in FIG. 26) is opened.

The "Method Properties" window 360, in an exemplary embodiment, includes, but is not limited to, a "use sample list" option 362, a "constant value" option 364, and a "use zone" option 366. The user may select one of the options. The "use sample list" option 362 allows the user to obtain the number of iterations for the method selected depending on the number of wells defined in the sample list. The "constant value" option 364 allows the user to specify the number of iterations for the method selected. This option is selected by default, in a preferred embodiment. The "use zone" option 366 allows the user to specify a zone. Additional options become available if the user selects the "use zone" option 366. The additional options may include, but are not limited to "use all wells in zone" option 368 or a "well count" option 370. The "use all wells in zone" option 368 allows the user to obtain the number of iterations for the method selected depending on the total number of wells defined for the zone in the bed layout. The "well count" option 370 allows the user to obtain the number of iterations for the method depending on the number of wells specified in a well count window 372.

The user may place any number of methods on the application builder workspace 340 in creating an application. Thus, the user can create a simple application consisting of a single method. Alternatively, the user can create a complex application comprised of a number of methods. The user may include multiple instances of the same method on the application builder workspace 340. The user places the methods on the application builder workspace 340 in the order that the methods should execute. After a user selects the "Save" button 348 or the "Save As" button 350, the created application is added to the application palette 336 for selection for editing, for modifying, for running, for simulating, etc. The application may also be added to the applications 126 of the database 122.

After creating an application, a simulation run 162 or an application run 164 can be executed. The simulation run 162 presents a graphical representation of an application run 162.

Figure 27:
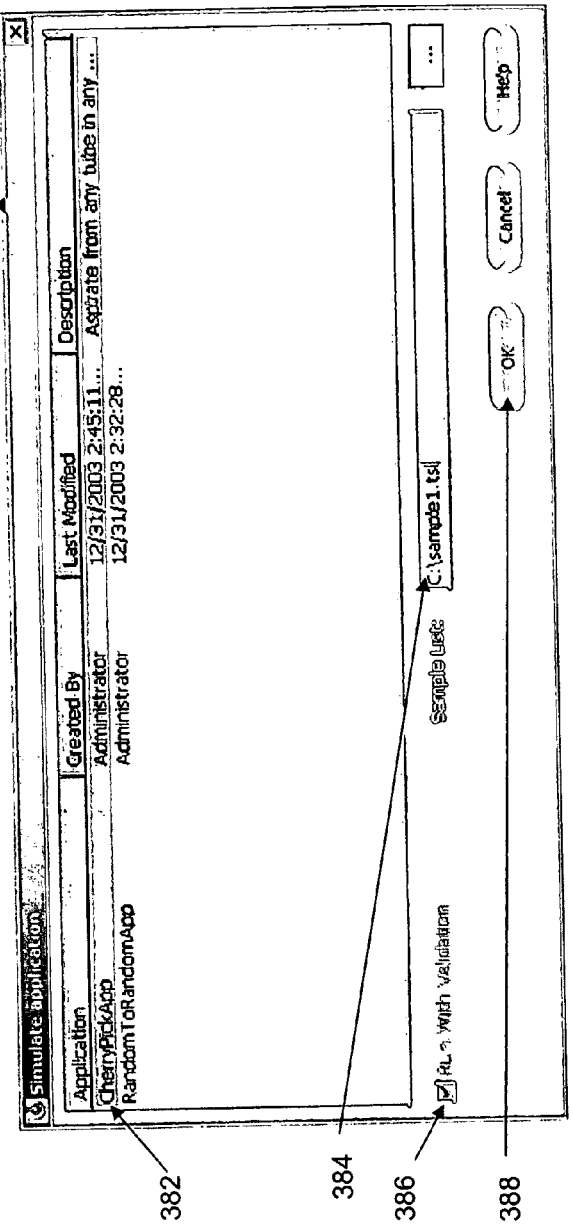
FIG. 27 depicts a user interface for defining a simulation of an application using the control application of FIG. 4 in an exemplary embodiment.

FIG. 27 shows a simulation user interface window 380 in an exemplary embodiment. The simulation user interface window 380 includes, but is not limited to, an application list 382, a sample list file selection window 384, a "run with validation" option 386, and an "OK" button 388 in an exemplary embodiment. The simulation user interface window 380 allows the user to select an application for simulation from the application list 382. The user may associate a sample list with the application using the sample list file selection window 384. If the "run with validation" option 386 is selected, the simulation run uses the physical constraints of the instruments as requirements. If the physical constraints are violated, an error message is created and the simulation run is stopped. If the "run with validation" option 386 is not selected, the simulation run does not impose the physical constraints of the instruments as requirements. If the physical constraints are violated, an error message is created, but the simulation run is not stopped. Selecting the "OK" button 388 starts the simulation run.

Figure 28:
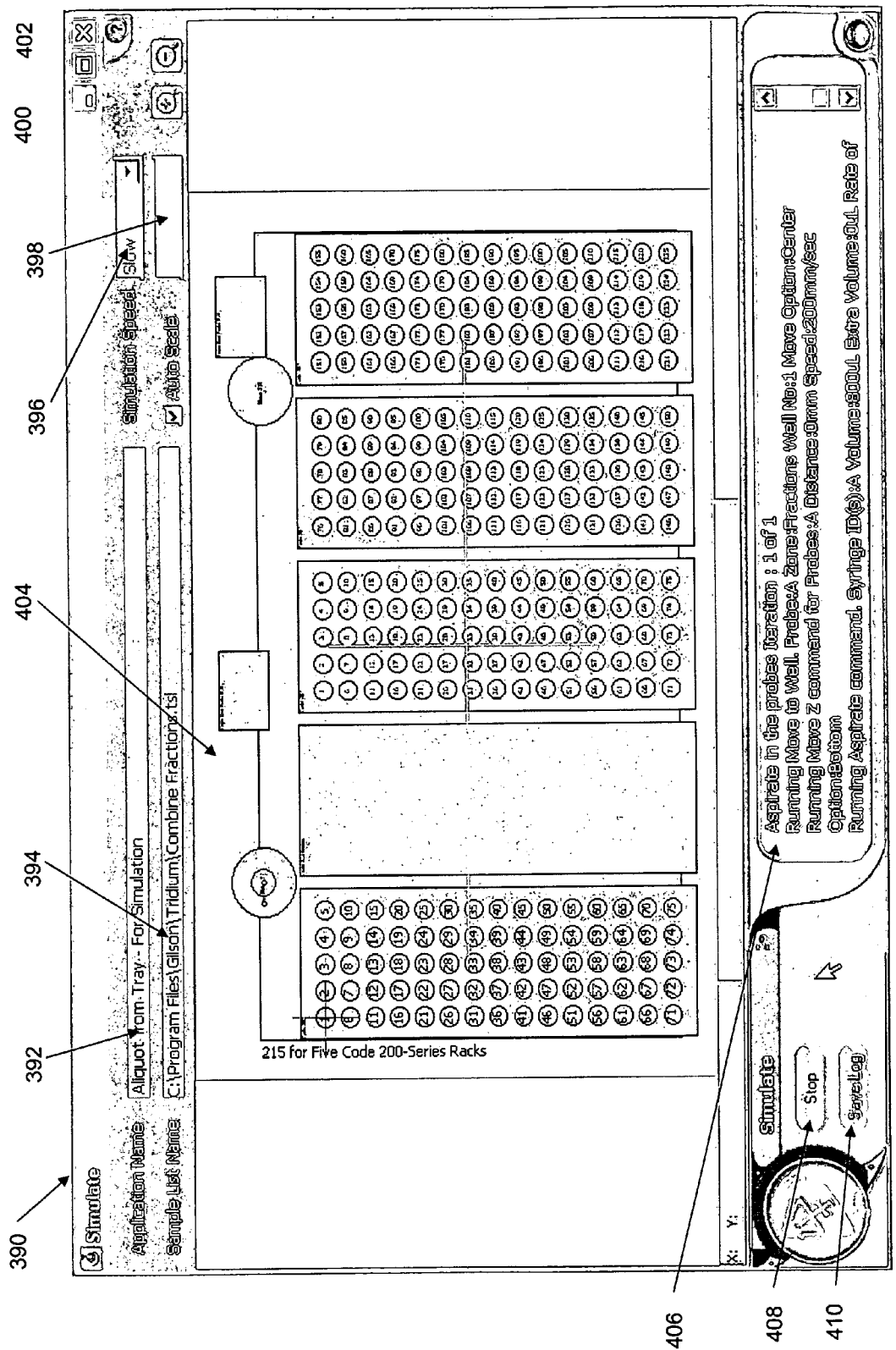
FIG. 28 depicts a simulation execution user interface of the control application of FIG. 4 in an exemplary embodiment.

FIG. 28 shows a simulation execution user interface window 390 in an exemplary embodiment. The user interface window 390 may include, but is not limited to, an application name display window 392, a sample list file display window 394, a simulation speed drop-down list 396, a view scale factor 398, a zoom in button 400, a zoom out button 402, a simulation execution view 404, a simulation status window 406, a "start/stop" button 408, and a "save log" button 410. The application name display window 392 displays the name of the application to simulate. The sample list file display window 394 displays the name of the sample list associated with the application simulation, if any. The simulation speed drop-down list 396 specifies the simulation speed and may be selectable by the user both before simulation execution and during the simulation execution in an exemplary embodiment. By adjusting the speed, the user may watch certain sections of the simulation in detail while stepping through other sections more quickly. In an exemplary embodiment, the user has three options: slow, medium, and high. Additional, fewer, or different speed levels may be provided.

The view scale factor 398 provides the scaling of the bed layout so that the user can adjust the simulation execution view 404 to see more or less detail. The scale factor may be selectable by the user both before simulation execution and during the simulation execution. The zoom in button 400 and the zoom out button 402 also allow the user to change the view of the simulation execution view 404 so that the user can see more or less detail. The simulation execution view 404 allows the user to see the actions performed during the simulation to ensure that the proper sequence of actions is executed prior to actually running the application using the instruments. The simulation status window 406 displays a detailed status of the executing simulation process and any error messages. The "start/stop" button 408 allows the user to toggle the simulation on and off. The simulation automatically stops when the simulation run is complete. The "save log" button 410 saves the simulation details to a LOG file for review later.

FIG. 29 shows an application run user interface window 380 in an exemplary embodiment. The simulation user interface window 420 includes, but is not limited to, an application list 422, a sample list file selection window 424, a "run with validation" option 426, and an "OK" button 428 in an exemplary embodiment. The application run interface window 420 allows the user to select an application for execution from the application list 422. The user may associate a sample list with the application using the sample list file selection window 424. If the "run with validation" option 426 is selected, the application run uses the physical constraints of the instruments as requirements. If the physical constraints are violated, an error message is created and the application run is stopped. If the "run with validation" option 426 is not selected, the application run does not impose the physical constraints of the instruments as requirements. If the physical constraints are violated, an error message is created, but the application run is not stopped. Selecting the "OK" button 428 starts the simulation run.

FIG. 30 shows a simulation execution user interface window 430 in an exemplary embodiment. The user interface window 430 may include, but is not limited to, an application name display window 432, a sample list file display window 434, an application run progress window 436, an application run log file window 438, a start button 440, a stop button 442, a pause button 444, and a "save log" button 446. The application name display window 432 displays the name of the application to run. The sample list file display window 434 displays the name of the sample list associated with the application run, if any. The application run progress window 436 displays the progress of the application run including the name and number of the executing method and the total number of methods defined for the application run. The application run log file window 438 displays more detailed information concerning the application run and current progress. The start button 440 starts the application run execution. The stop button 442 stops the application run execution. The pause button 444 pauses the application run execution. Pressing the pause button 444 again restarts the application run at the currently executing command. The "save log" button 446 saves the application run details to a .LOG file for review later.

Figures 31, 32:
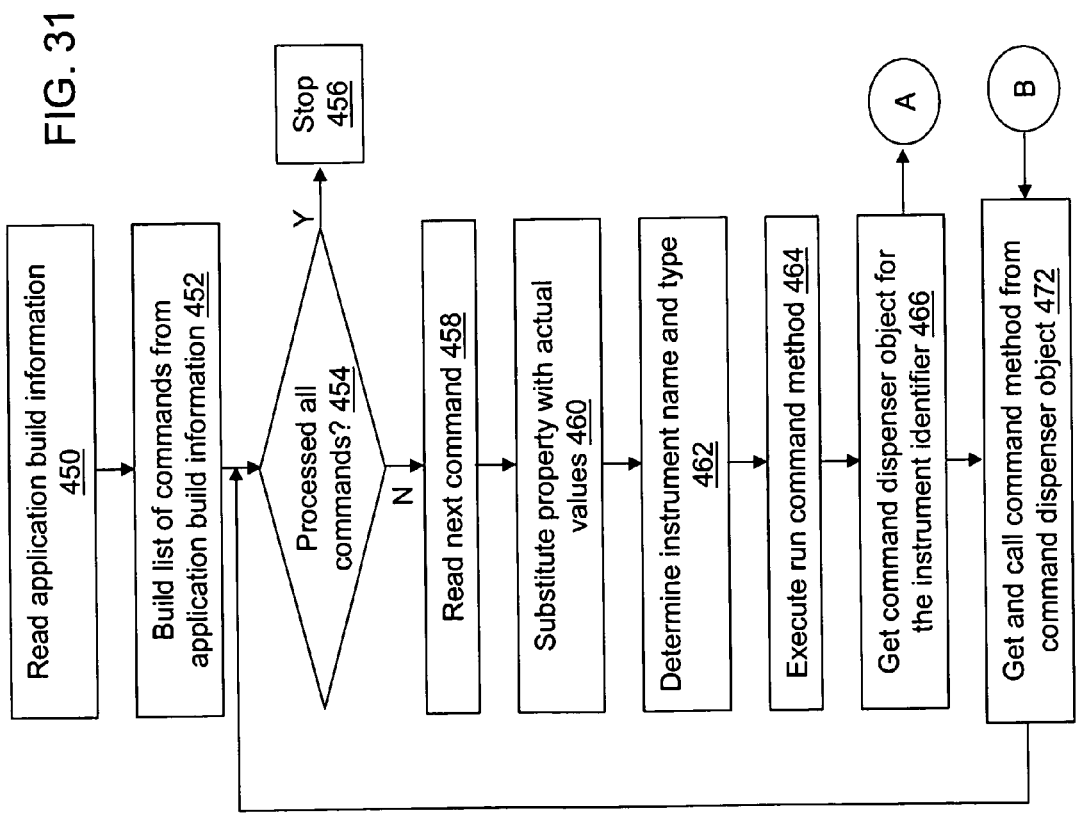
FIG. 31 is a flow diagram of command processing for the control application of FIG. 4 in an exemplary embodiment.
FIG. 32 is a flow diagram of command selection based on the instrument name and type of the control application of FIG. 4 in an exemplary embodiment.

In an exemplary embodiment, the build 154 process outlined above may execute in a different thread from the run 156 process that may be a simulation run 162 or an application run 164. The multiple threads may be synchronized with each other in a preferred embodiment. After the user completes the build process for the application and possibly simulates the built application either with or without validation of the simulation run, the application is ready to execute. The application may be executed without a simulation run 162, but in a preferred embodiment, the simulation run 162 is executed before the application run 164. With reference to FIG. 31, when the application run 164 is selected from the main menu 152 of the control application 124, the control application 124 reads the application build information at operation 450. Build information includes, but is not limited to, the configuration, the bed layout, the tasks, the sample list, and the methods. At operation 452, the control application 124 builds a list of commands to run from the build information. The control application 124 processes each command in the order defined from the build information.

The decision at operation 454 determines if the control application 124 has processed all of the commands in the list of commands created from the build information. If the control application 124 has processed all of the commands, the application run 164 stops at operation 456. If the control application 124 has not processed all of the commands, the control application 124 reads the command properties of the next command at operation 458. The control application 124 maintains a list of command properties and of command property values in a table. While processing the command, the command property value is substituted for the corresponding command property at operation 460. At operation 462, the control application 124 determines the name and the type of instrument to perform the command. At operation 464, the "run command" method is executed. The "run command" method accepts calling parameters. In an example embodiment, the calling parameters include, but are not limited to, a command name, an instrument name, an instrument type, and a parameter list for the command based on the command name. The command name identifies the command type to execute. Because the command may be implemented differently depending on the instrument that executes the command, the instrument name and/or the instrument type identify the specific implementation of the command to select for execution. As such the instrument name and/or the instrument type may define an instrument identifier. The parameter list for the command generally corresponds to the command property values defined for the command type during the application build. The parameter list for the command is a "super-set" of the parameters required for that command for any instrument type because the command is a generic command. A generic command is used so that the "run command" method may interface with all instances of the command despite differences that may result based on the configuration of device 104.

At operation 466, the "run command" method of the control application 124 gets a command dispenser object for the instrument name and/or instrument type from the driver interface 118. The command dispenser object specific to the instrument includes a method for executing each command defined for the instrument. All of the translator logic and control calls specific to an instrument type are implemented within the methods of the command dispenser object. For example, the MoveTo command accepts six calling parameters in the "run command" method. The QuadZ 215 instrument MoveTo command implemented in the command dispenser object accepts all six calling parameters but ignores the second and fourth calling parameters because the QuadZ 215 instrument does not require these parameters. However, the Constellation instrument MoveTo command implementation requires all six calling parameters for proper operation of the instrument. These details are encapsulated in the command dispenser object for the Constellation instrument. At operation 472, the control application 124 gets and calls the command method defined in the command dispenser object that corresponds to the command name passed through the calling structure of the "run command" method. Processing continues with the next command at operation 454.

To get the command dispenser object for the specified instrument name, at operation 468, the control application 124 searches a collection of created command dispenser objects using the instrument name. The decision at operation 470 determines if a matching instrument name is found in the collection of created command dispenser objects. If a matching instrument name is found, the run command method gets the command dispenser object that corresponds to the matching instrument name. At operation 472, the run command method executes the command dispenser object command method.

If a matching instrument name is not found in the collection of created command dispenser objects, the control application 124 searches the database 122 using the instrument type at operation 474. Instrument information found in the database 122 for the instrument type is selected from the database 122 at operation 476. At operation 478, the loaded instrument information is used to create a new command dispenser object for the instrument name. At operation 450, the new command dispenser object is added to the collection of created command dispenser objects. The "run command" method gets the new command dispenser object. At operation 472, the "run command" method executes the new command dispenser object command method.

The above described control application 124 provides the user with instrument control software that is modular and flexible and provides for user defined and customizable commands, tasks, methods, and applications that can control multiple diverse devices 104. The above described control application 124 further provides the user with the ability to assign a target to multiple zones on a bed layout. Additionally, the above described control application 124 provides the user with the capability to both simulate and execute application runs that do not conform to the physical constraints of the device 104 allowing the user to modify the device 104 while permitting continued use of the control application 124.

It is understood that the invention is not confined to the particular embodiments set forth herein as illustrative, but embraces all such modifications, combinations, and permutations as come within the scope of the following claims. The description above focused on an preferred embodiment of the invention designed to operate on a computer system executing a Microsoft® Windows based operating system. The present invention, however, is not limited to a particular operating environment. Those skilled in the art will recognize that the system and methods of the present invention may be advantageously operated on different platforms using different operating systems including but not limited to the Macintosh® operating system or UNIX® based operating systems. Additionally, the functionality described may be distributed among modules that differ in number and distribution of functionality from those described herein without deviating from the spirit of the invention. Additionally, the order of execution of the modules may be changed without deviating from the spirit of the invention. Thus, the description of the preferred embodiments is for purposes of illustration and not limitation.

What is claimed is:

1. A controller for controlling a sequence of actions at a device, the controller comprising:
    a control application including computer-readable instructions, wherein the computer-readable instructions are configured to cause the controller to
        receive a first user input that identifies an instrument component in a bed layout of a device, wherein the bed layout defines an arrangement of a plurality of instrument components;
        receive a second user input that assigns the identified instrument component to a first zone of the bed layout, wherein the first zone identifies a first group of one or more instrument components of the plurality of instrument components at which to perform a first type of action;
        receive a third user input that assigns the identified instrument component to a second zone of the bed layout, wherein the second zone identifies a second group of one or more instrument components of the plurality of instrument components at which to perform a second type of action; and
        receive command information associated with an action of the first type of action for an instrument of the device to perform, wherein the command information comprises
            a command name, the command name identifying the action; and
            a device identifier, the device identifier identifying the instrument;
        identify a unique command method corresponding to the device identifier and to the command name, the identified unique command method including instructions to control the action for the instrument to perform;
        receive a fourth user input that indicates an operational mode for controlling performance of the action, wherein the operational mode includes a non-validation mode, the non-validation mode defining a state of operation wherein a device limitation is not imposed to restrict the action;

select a device driver based on the device identifier;

execute the identified unique command method to generate control commands for causing execution of the action at the instrument; and communicate the generated control commands to the selected device driver to control execution of the action at the instrument on the identified instrument component without imposing the device limitation if the fourth user input indicates the non-validation mode;

a memory, the memory storing the control application; and a processor, the processor coupled to the memory and configured to execute the control application.

2. A controller for controlling a device, wherein the device supports assignment of a target to a plurality of zones in a bed layout of the device, the controller comprising:

a control application including computer-readable instructions, wherein the computer-readable instructions are configured to cause the controller to receive a first user input that identifies an instrument component in a bed layout of a device, wherein the bed layout defines an arrangement of a plurality of instrument components;

receive a second user input that assigns the identified instrument component to a first zone of the bed layout, wherein the first zone identifies a first group of one or more instrument components of the plurality of instrument components at which to perform a first type of action;

receive a third user input that assigns the identified instrument component to a second zone of the bed layout, wherein the second zone identifies a second group of one or more instrument components of the plurality of instrument components at which to perform a second type of action;

receive a fourth user input that indicates an operational mode for controlling performance of an action associated with one of the first type of action and the second type of action, wherein the operational mode includes a non-validation mode, the non-validation mode defining a state of operation wherein a device limitation is not imposed to restrict the action; and control operation of the device as it performs the first type of action at the identified instrument component and the second type of action at the identified instrument component without imposing the device limitation if the fourth user input indicates the non-validation mode;

a memory, the memory storing the control application; and a processor, the processor coupled to the memory and configured to execute the control application.

3. The controller of claim 2 wherein the first type of action is an action selected from the group consisting of aspirate, eject, home, move, and dispense.

4. The controller of claim 2 wherein the identified instrument component is a device component selected from the group consisting of a tube, a vial, a spot, a well, an injection port, a rinse station, a microplate, a reservoir, and a handle.

5. The controller of claim 2 wherein the instrument is selected from the group consisting of a dilutor, a pump, a liquid handler, a fraction collector, a detector, an injector, a sampler, a dispenser, and a liquid chromatographer.

6. The controller of claim 2 wherein the first type of action and the second type of action are the same.

7. The controller of claim 2 further comprising a display, wherein the display is configured to provide a visual representation of the bed layout with the first zone.

8. The controller of claim 2 wherein the bed layout includes a plurality of instruments.

9. A method of controlling a device, wherein the device supports assignment of a target to a plurality of zones in a bed layout of the device, the method comprising:

receiving a first user input that identifies an instrument component in a bed layout of a device in a controller of the device, wherein the bed layout defines an arrangement of a plurality of instrument components;

in the controller of the device, receiving a second user input that assigns the identified instrument component to a first zone of the bed layout, wherein the first zone identifies a first group of one or more instrument components of the plurality of instrument components at which to perform a first type of action;

in the controller of the device, receiving a third user input that assigns the identified instrument component to a second zone of the bed layout, wherein the second zone identifies a second group of one or more instrument components of the plurality of instrument components at which to perform a second type of action;

receiving a fourth user input that indicates an operational mode for controlling performance of an action associated with one of the first type of action and the second type of action, wherein the operational mode includes a non-validation mode, the non-validation mode defining a state of operation wherein a device limitation is not imposed to restrict the action; and controlling the device to perform the first type of action at the identified instrument component and the second type of action at the identified instrument component using the controller without imposing the device limitation if the fourth user input indicates the non-validation mode.

10. A non-transitory computer-readable medium having computer-readable instructions stored thereon that, if executed by a processor, cause the processor to perform operations comprising:

receiving a first user input that identifies an instrument component in a bed layout of a device, wherein the bed layout defines an arrangement of a plurality of instrument components;

receiving a second user input that assigns the identified instrument component to a first zone of the bed layout, wherein the first zone identifies a first group of one or more instrument components of the plurality of instrument components at which to perform a first type of action;

receiving a third user input that assigns the identified instrument component to a second zone of the bed layout, wherein the second zone identifies a second group of one or more instrument components of the plurality of instrument components at which to perform a second type of action;

receiving a fourth user input that indicates an operational mode for controlling performance of an action associated with one of the first type of action and the second type of action, wherein the operational mode includes a non-validation mode, the non-validation mode defining a state of operation wherein a device limitation is not imposed to restrict the action; and controlling the device as it performs the first type of action at the identified instrument component and the second type of action at the identified instrument component without imposing the device limitation if the fourth user input indicates the non-validation mode.

11. A system for controlling a device, wherein the device supports assignment of a target to a plurality of zones in a bed layout of the device, the system comprising:
a device; and
a controller, the controller comprising
a control application including computer-readable instructions, wherein the computer-readable instructions are configured to cause the controller to
receive a first user input that identifies an instrument component in a bed layout of a device, wherein the bed layout defines an arrangement of a plurality of instrument components;
receive a second user input that assigns the identified instrument component to a first zone of the bed layout, wherein the first zone identifies a first group of one or more instrument components of the plurality of instrument components at which to perform a first type of action;
receive a third user input that assigns the identified instrument component to a second zone of the bed layout, wherein the second zone identifies a second group of one or more instrument components of the plurality of instrument components at which to perform a second type of action;
receive a fourth user input that indicates an operational mode for controlling performance of an action associated with one of the first type of action and the second type of action, wherein the operational mode includes a non-validation mode, the non-validation mode defining a state of operation wherein a device limitation is not imposed to restrict the action; and
control operation of the device as it performs the first type of action at the identified instrument component and the second type of action at the identified instrument component without imposing the device limitation if the fourth user input indicates the non-validation mode;
a memory, the memory storing the control application; and
a processor, the processor coupled to the memory and configured to execute the control application.

12. A controller for providing device independent commands to a device, the controller comprising:
a driver interface including computer-readable instructions, wherein the computer-readable instructions are configured to cause the controller to
receive command information associated with an action for a device to perform, wherein the command information comprises
a command name, the command name identifying the action;
a device identifier, the device identifier identifying the device; and
a mode indicator, the mode indicator indicating an operational mode, wherein the operational mode includes a non-validation mode defining a state of operation wherein a device limitation is not imposed to restrict the action;
identify a unique command method corresponding to the device identifier and to the command name, the identified unique command method including instructions to control the action for the device to perform without imposing the device limitation if the non-validation mode is indicated;
select a device driver based on the device identifier;
execute the identified unique command method to generate control commands for causing execution of the action by the device; and
communicate the generated control commands to the selected device driver to control execution of the action by the device without imposing the device limitation if the mode indicator indicates the non-validation mode;
a memory, the memory storing the driver interface; and
a processor, the processor coupled to the memory and configured to execute the driver interface.

13. The controller of claim 12 wherein the device is selected from the group consisting of a dilutor, a pump, a liquid handler, a fraction collector, a detector, an injector, a sampler, a dispenser, and a liquid chromatographer.

14. The controller of claim 12 wherein identifying the unique command method comprises executing a computer method, wherein the computer method receives the command information.

15. The controller of claim 12 wherein identifying the unique command method comprises:
getting a command dispenser object using the device identifier, the command dispenser object including a plurality of control calls specific to the device; and
getting the identified unique command method that corresponds to the command name from the command dispenser object.

16. The controller of claim 15 wherein getting the command dispenser object comprises:
searching a collection of command dispenser objects using the device identifier;
selecting the command dispenser object that matches the device identifier.

17. The controller of claim 15 wherein getting the command dispenser object comprises:
searching a database using the device identifier;
selecting device information from the database that matches the device identifier; and
creating a new command dispenser object for the device using the device information selected from the database.

18. The controller of claim 17 wherein the computer-readable instructions are further configured to cause the controller to add the new command dispenser object to a collection of command dispenser objects using the device identifier.

19. The controller of claim 12 wherein the command information further comprises a command property value, wherein the command property value is associated with a property of the action.

20. A method of providing device independent commands for a device, the method comprising:
receiving command information associated with an action for a device to perform, wherein the command information comprises
a command name, the command name identifying the action;
a device identifier, the device identifier identifying the device; and
a mode indicator, the mode indicator indicating an operational mode, wherein the operational mode includes a non-validation mode defining a state of operation wherein a device limitation is not imposed to restrict the action;

a controller identifying a unique command method corresponding to the device identifier and to the command name, the identified unique command method including instructions to control the action for the device to perform;
a controller selecting a device driver based on the device identifier;
a controller executing the identified unique command method to generate control commands for causing execution of the action by the device; and
a controller communicating the generated control commands to the selected device driver to control execution of the action by the device without imposing the device limitation if the mode indicator indicates the non-validation mode.

21. A non-transitory computer-readable medium having computer-readable instructions stored thereon that, if executed by a processor, cause the processor to perform operations comprising:
receiving command information associated with an action for a device to perform, wherein the command information comprises:
a command name, the command name identifying the action;
a device identifier, the device identifier identifying the device; and
a mode indicator, the mode indicator indicating an operational mode, wherein the operational mode includes a non-validation mode defining a state of operation wherein a device limitation is not imposed to restrict the action;
identifying a unique command method corresponding to the device identifier and to the command name, the identified unique command method including instructions to control the action for the device to perform without imposing the device limitation if the non-validation mode is indicated;
selecting a device driver based on the device identifier;
executing the identified unique command method to generate control commands for causing execution of the action by the device; and
communicating the generated control commands to the selected device driver to control execution of the action by the device without imposing the device limitation if the mode indicator indicates the non-validation mode.

22. A system for providing device independent commands to a device, the system comprising:
a device;
a controller, the controller comprising
a driver interface including computer-readable instructions, wherein the computer-readable instructions are configured to cause the controller to
receive command information associated with an action for the device to perform, wherein the command information comprises
a command name, the command name identifying the action;
a device identifier, the device identifier identifying the device; and
a mode indicator, the mode indicator indicating an operational mode, wherein the operational mode includes a non-validation mode defining a state of operation wherein a device limitation is not imposed to restrict the action;
identify a unique command method corresponding to the device identifier and to the command name, the identified unique command method including instructions to control the action for the device to perform without imposing the device limitation if the mode indicator indicates the non-validation mode;
select a device driver based on the device identifier;
execute the identified unique command method to generate control commands for causing execution of the action by the device; and
communicate the generated control commands to the selected device driver to control execution of the action by the device without imposing the device limitation if the mode indicator indicates the non-validation mode;
a memory, the memory storing the driver interface; and
a processor, the processor coupled to the memory and configured to execute the driver interface; and
the selected device driver, wherein the selected device driver is configured to support communication between the controller and the device and to translate the generated control commands for execution by the device.

23. A controller operating a device in an atypical mode of operation, the controller comprising:
a control application including computer-readable instructions, wherein the computer-readable instructions are configured to cause the controller to
receive a first user input that defines an application, wherein execution of the defined application causes a device to perform a sequence of actions;
receive a second user input that indicates an operational mode for executing the defined application, wherein the operational mode includes a non-validation mode, the non-validation mode defining a state of operation of the defined application wherein a limitation of the device is not imposed to restrict the sequence of actions, wherein if the non-validation mode is not indicated, the computer-readable instructions are configured to cause the controller to create an error message if the device limitation is violated; and
execute the sequence of actions without imposing the device limitation if the second user input indicates the non-validation mode;
a memory, the memory storing the control application; and
a processor, the processor coupled to the memory and configured to execute the control application.

24. The controller of claim 23 wherein the device is selected from the group consisting of a dilutor, a pump, a liquid handler, a fraction collector, a detector, an injector, a sampler, a dispenser, and a liquid chromatographer.

25. A method of operating a device in an atypical mode of operation, the method comprising:
receiving a first user input that defines an application at a controller, wherein execution of the defined application causes a device to perform a sequence of actions;
receiving a second user input that indicates an operational mode for executing the defined application at the controller, wherein the operational mode includes a non-validation mode, the non-validation mode defining a state of operation of the defined application wherein a limitation of the device is not imposed to restrict the sequence of actions, wherein if the non-validation mode is not indicated, an error message is created by the controller if the device limitation is violated; and
the controller executing the sequence of actions without imposing the device limitation if the second user input indicates the non-validation mode.

26. A non-transitory computer-readable medium having computer-readable instructions stored thereon that, if executed by a processor, cause the processor to perform a method comprising:
    receiving a first user input that defines an application, wherein execution of the defined application causes a device to perform a sequence of actions;
    receiving a second user input that indicates an operational mode for executing the defined application, wherein the operational mode includes a non-validation mode, the non-validation mode defining a state of operation of the defined application wherein a device limitation is not imposed to restrict the sequence of actions, wherein if the non-validation mode is not indicated, the computer-readable instructions are configured to cause the controller to create an error message if the device limitation is violated; and
    executing the sequence of actions without imposing the device limitation if the second user input indicates the non-validation mode.

27. A system for operating a device in an atypical mode of operation, the system comprising:
    a device; and
    a controller, the controller comprising
        a control application including computer-readable instructions, wherein the computer-readable instructions are configured to cause the controller to
            receive a first user input that defines an application, wherein execution of the defined application causes the device to perform a sequence of actions;
            receive a second user input that indicates an operational mode for executing the defined application, wherein the operational mode includes a non-validation mode, the non-validation mode defining a state of operation of the defined application wherein a limitation of the device is not imposed to restrict the sequence of actions, wherein if the non-validation mode is not indicated, the computer-readable instructions are configured to cause the controller to create an error message if the device limitation is violated; and
            execute the sequence of actions without imposing the device limitation if the second user input indicates the non-validation mode;
    a memory, the memory storing the control application; and
    a processor, the processor coupled to the memory and configured to execute the control application.

* * * * *